US012049886B2

(12) United States Patent
Macari et al.

(10) Patent No.: US 12,049,886 B2
(45) Date of Patent: *Jul. 30, 2024

(54) UTERINE DISTENSION FLUID MANAGEMENT SYSTEM WITH PERISTALTIC PUMPS

(71) Applicant: HOLOGIC, INC., Marlborough, MA (US)

(72) Inventors: Danny Macari, Sudbury, MA (US); Mathew John Whitney, Uxbridge, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/061,418

(22) Filed: Dec. 2, 2022

(65) Prior Publication Data

US 2023/0096757 A1    Mar. 30, 2023

Related U.S. Application Data

(63) Continuation of application No. 17/317,432, filed on May 11, 2021, now Pat. No. 11,525,440, which is a (Continued)

(51) Int. Cl.
*F04B 43/12*    (2006.01)
*A61M 3/02*    (2006.01)
(Continued)

(52) U.S. Cl.
CPC ....... *F04B 43/1276* (2013.01); *A61M 3/0201* (2021.05); *A61M 3/0258* (2013.01);
(Continued)

(58) Field of Classification Search
CPC ............. F04B 43/0072; F04B 43/1253; F04B 43/1276; F04B 43/1292; F04B 53/16;
(Continued)

(56) References Cited

U.S. PATENT DOCUMENTS 3,447,478 A    6/1969  Clemens et al.
3,841,799 A   10/1974  Spinosa et al.
(Continued)

FOREIGN PATENT DOCUMENTS

WO    1991016542 A1    10/1991
WO    2006/024192 A1    3/2006
(Continued)

OTHER PUBLICATIONS

Internet pages and product information concerning Welco WP1000 / WP1100 High Performance Peristaltic Pump, WELCO Co., Ltd., accessed on Nov. 2015 at http://www.welco.net. (2 pages).
(Continued)

*Primary Examiner* — Philip E Stimpert
(74) *Attorney, Agent, or Firm* — Vista IP Law Group, LLP

(57) ABSTRACT

A pump cartridge for mounting on a drive rotor includes a roller assembly having first and second hubs maintained in a spaced apart relationship and defining an axis, and a plurality of planetary rollers arranged in a circumferentially spaced orientation about the axis, the rollers mounted to the hubs displacement radially outward. One or more compressible tubing lines are interposed between the rollers and an interior wall of the pump cartridge housing. The housing and the first and second hubs collectively define a passageway through which a spreader on the drive rotor extends and may be rotated relative to the roller assembly to displace the rollers radially outward to thereby compress the tubing lines against the interior wall. A coupling feature on the first hub engages a roller driving feature of the rotor, so that rotation of the rotor causes rotation of the roller assembly about the axis.

17 Claims, 21 Drawing Sheets

Related U.S. Application Data continuation of application No. 16/133,510, filed on Sep. 17, 2018, now Pat. No. 11,009,021, which is a continuation of application No. 15/389,403, filed on Dec. 22, 2016, now Pat. No. 10,077,767.

(60) Provisional application No. 62/387,390, filed on Dec. 24, 2015.

(51) Int. Cl.
| | |
|---|---|
| *F04B 43/00* | (2006.01) |
| *F04B 43/08* | (2006.01) |
| *F04B 43/09* | (2006.01) |
| *F04B 53/16* | (2006.01) |
| *A61B 17/32* | (2006.01) |
| *A61B 17/3203* | (2006.01) |
| *A61B 17/42* | (2006.01) |
| *A61B 50/13* | (2016.01) |
| *A61M 1/00* | (2006.01) |
| *A61M 29/00* | (2006.01) |

(52) U.S. Cl.
CPC ...... *F04B 43/0072* (2013.01); *F04B 43/1253* (2013.01); *F04B 43/1292* (2013.01); *F04B 53/16* (2013.01); *A61B 17/32* (2013.01); *A61B 17/3203* (2013.01); *A61B 17/42* (2013.01); *A61B 2017/4216* (2013.01); *A61B 50/13* (2016.02); *A61M 1/77* (2021.05); *A61M 29/00* (2013.01); *A61M 2205/12* (2013.01); *F04B 43/08* (2013.01); *F04B 43/09* (2013.01)

(58) Field of Classification Search
CPC .... A61M 1/0058; A61M 1/77; A61M 3/0201; A61M 3/0258; A61M 2205/12
USPC ............................................ 417/477.7, 477.8
See application file for complete search history.

(56) References Cited

U.S. PATENT DOCUMENTS

| | | | |
|---|---|---|---|
| 3,927,955 | A | 12/1975 | Spinosa et al. |
| 4,138,205 | A | 2/1979 | Wallach |
| 4,179,249 | A | 12/1979 | Guttmann |
| 4,537,561 | A | 8/1985 | Xanthopoulos |
| 4,673,334 | A | 6/1987 | Allington et al. |
| 4,702,679 | A | 10/1987 | Malbec |
| 4,735,558 | A | 4/1988 | Kienholz et al. |
| 4,798,580 | A | 1/1989 | DeMeo et al. |
| 4,904,168 | A | 2/1990 | Cavoto et al. |
| 5,044,902 | A | 9/1991 | Malbec |
| 5,266,013 | A | 11/1993 | Aubert et al. |
| 5,340,290 | A | 8/1994 | Clemens |
| 5,356,267 | A | 10/1994 | Fulmer |
| 5,433,588 | A | 7/1995 | Monk et al. |
| 5,586,872 | A | 12/1996 | Skobelev et al. |
| 5,588,815 | A | 12/1996 | Zaleski, II |
| 5,741,125 | A | 4/1998 | Neftel et al. |
| 5,927,956 | A | 7/1999 | Lim et al. |
| 6,082,977 | A | 7/2000 | Nishioka |
| 6,468,059 | B2 | 10/2002 | Haser et al. |
| 6,733,476 | B2 | 5/2004 | Christenson et al. |
| 6,896,664 | B2 | 5/2005 | Novak |
| 7,252,485 | B2 * | 8/2007 | Ito ...................... F04B 43/1253 417/477.3 |
| 7,445,436 | B2 | 11/2008 | Mittelstein et al. |
| 7,467,932 | B2 | 12/2008 | Schann et al. |
| 7,591,639 | B2 | 9/2009 | Kent |
| 7,934,912 | B2 | 5/2011 | Voltenburg, Jr. et al. |
| 8,152,268 | B2 | 4/2012 | Watanabe |
| 8,297,956 | B2 | 10/2012 | Neftel et al. |
| 8,377,001 | B2 | 2/2013 | Pfouts et al. |
| 8,459,968 | B2 | 6/2013 | Juretich et al. |
| 8,491,285 | B2 | 7/2013 | Haser et al. |
| 8,876,489 | B2 | 11/2014 | Shener |
| 9,084,847 | B2 | 7/2015 | Klein et al. |
| 9,140,251 | B2 | 9/2015 | Beiriger |
| 2005/0238516 | A1 | 10/2005 | Kent |
| 2007/0098579 | A1 | 5/2007 | Boukhny et al. |
| 2011/0300010 | A1 | 12/2011 | Jarnagin et al. |
| 2012/0175292 | A1 | 7/2012 | Beiriger |
| 2013/0037142 | A1 | 2/2013 | Farrell |
| 2013/0343938 | A1 | 12/2013 | Hutchison et al. |
| 2014/0301866 | A1 | 10/2014 | Neftel |
| 2014/0322054 | A1 | 10/2014 | Bach et al. |

FOREIGN PATENT DOCUMENTS

| | | |
|---|---|---|
| WO | 2009042192 A1 | 4/2009 |
| WO | 2013190388 A2 | 12/2013 |
| WO | 2014/164655 A1 | 10/2014 |

OTHER PUBLICATIONS

PCT International Search Report and Written Opinion for International Appln. No. PCT/US2016/068457, Applicant Hologic, Inc., forms PCT/ISA/210, 220, and 237, dated Mar. 21, 2017 (13 pages).

* cited by examiner

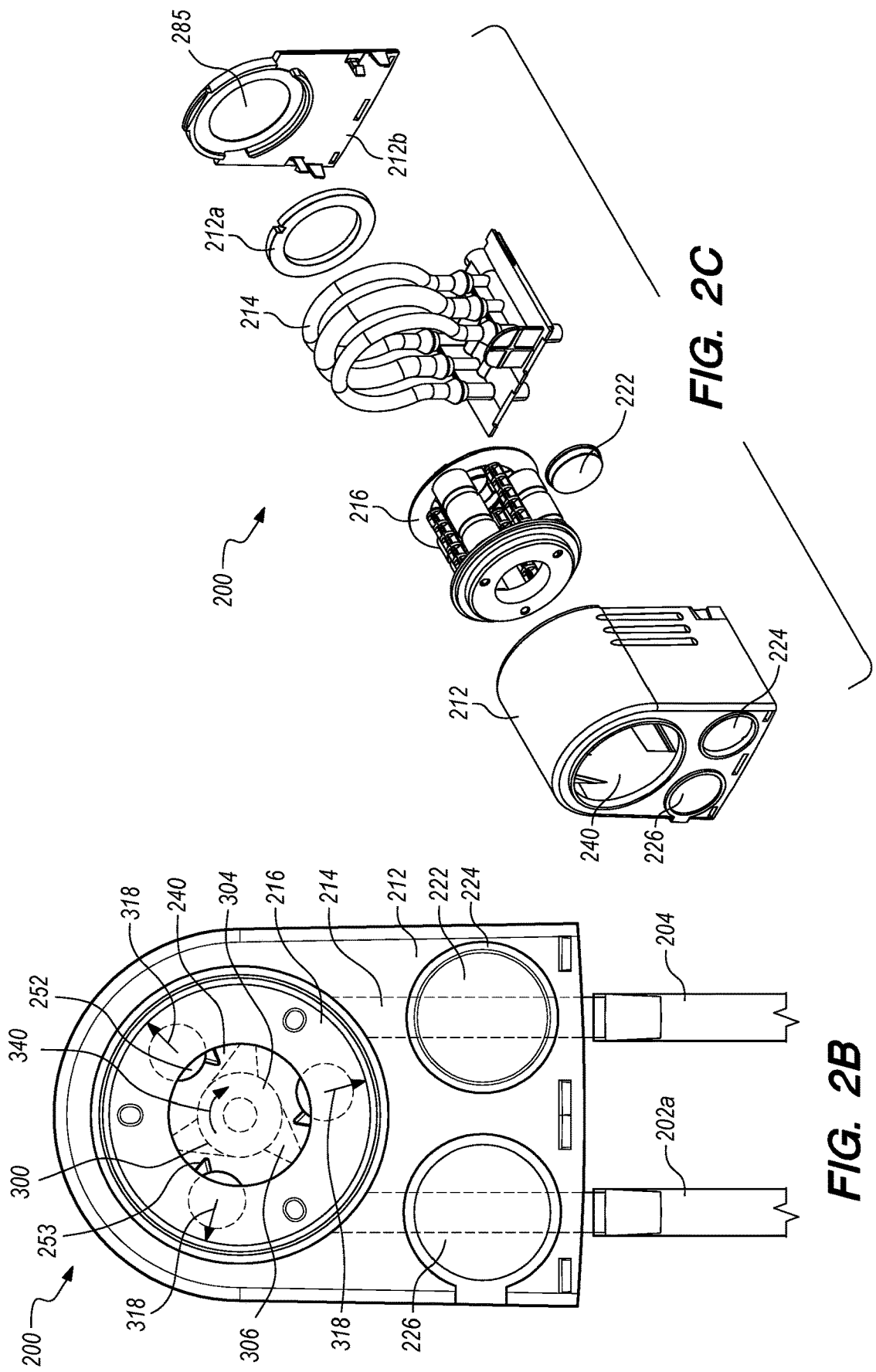

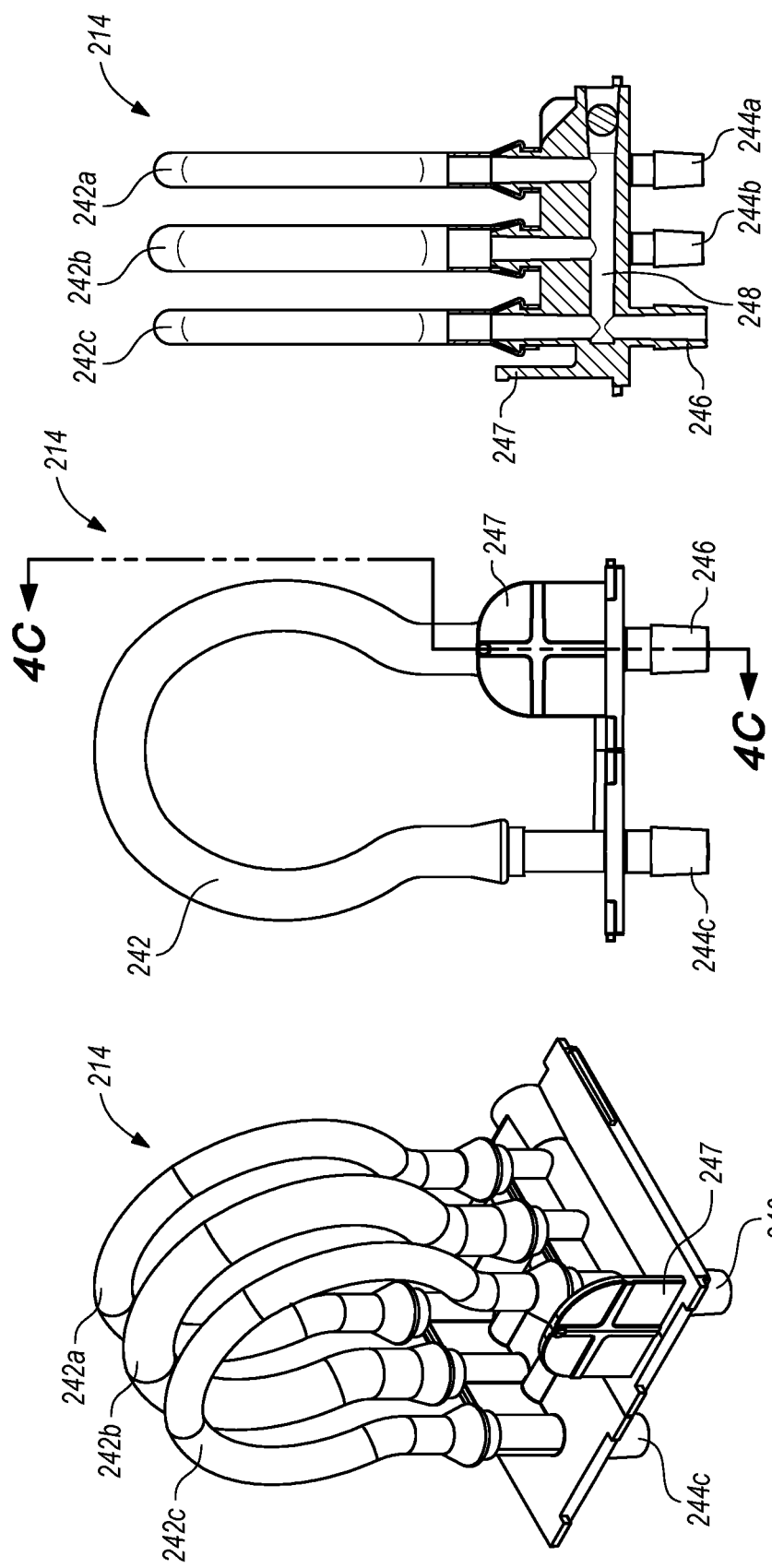

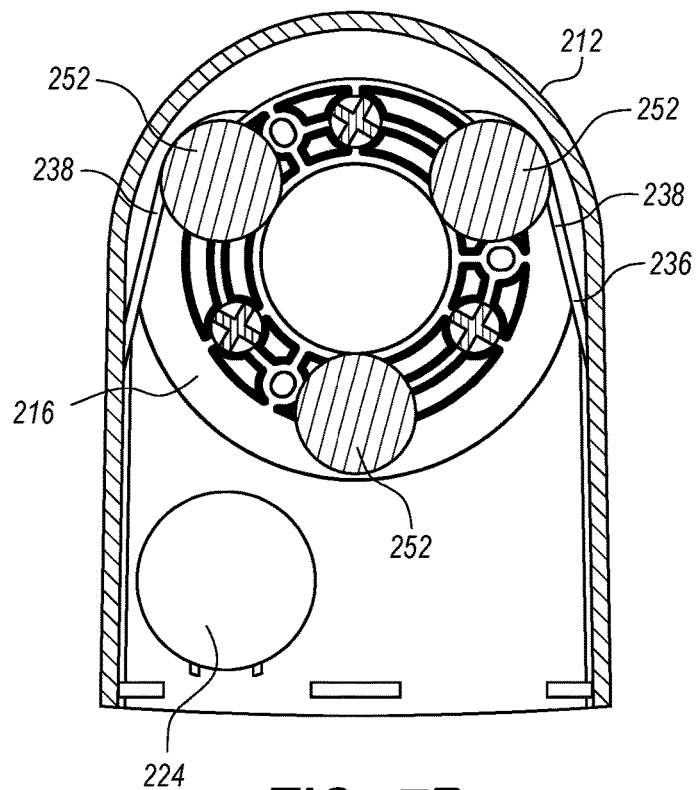
FIG. 7B
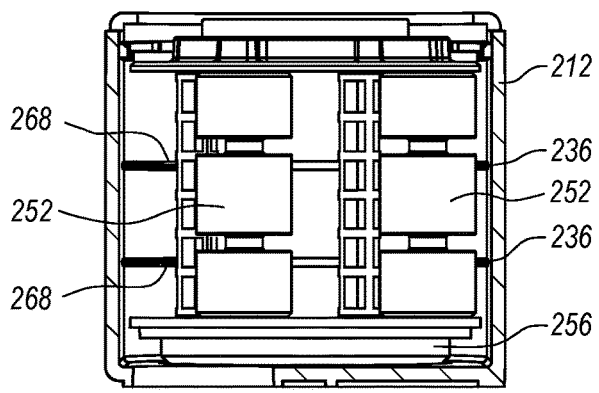 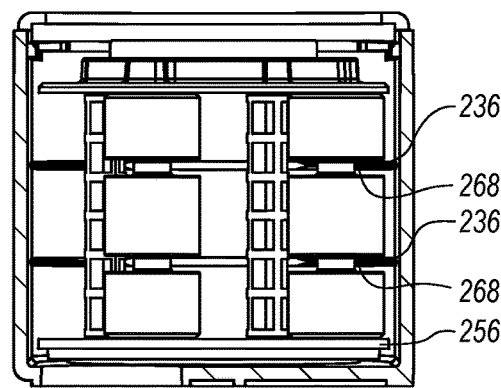
FIG. 7C  FIG. 7D

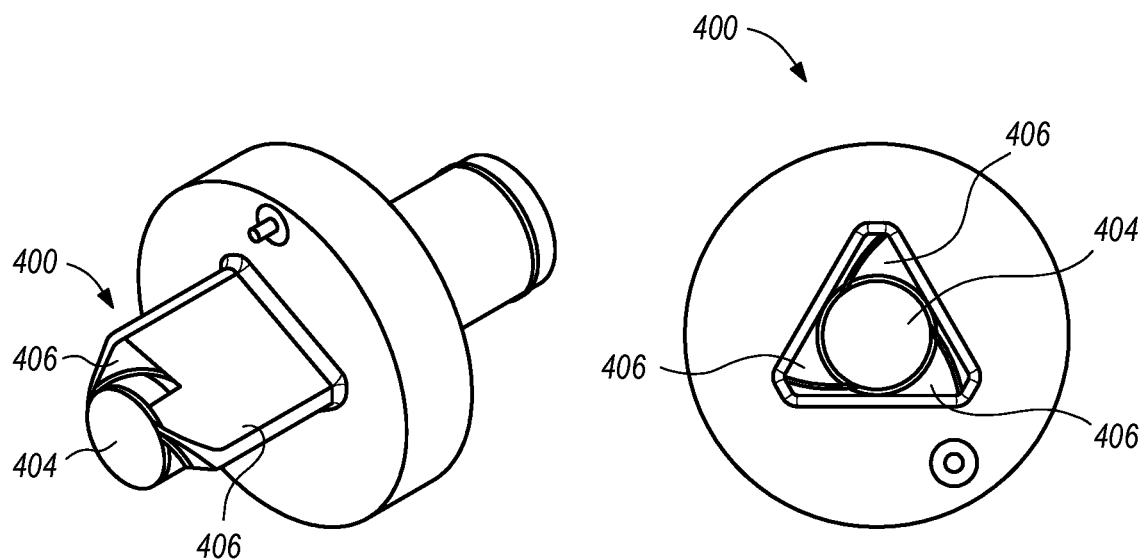
FIG. 10A  FIG. 10B
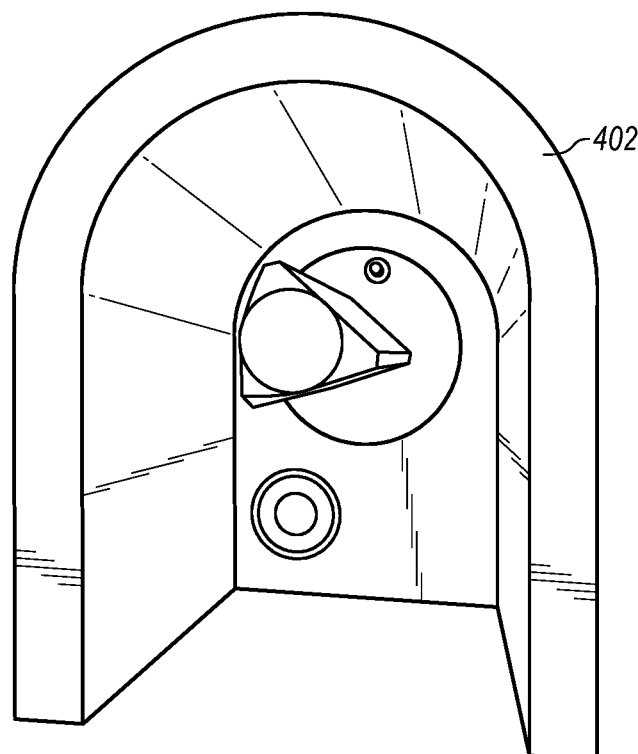
FIG. 11

UTERINE DISTENSION FLUID MANAGEMENT SYSTEM WITH PERISTALTIC PUMPS

RELATED APPLICATIONS DATA

The present application is a continuation of U.S. patent application Ser. No. 17/317,432, filed May 11, 2021, now U.S. Pat. No. 11,525,440, which is a continuation of U.S. patent application Ser. No. 16/133,510, filed Sep. 17, 2018, now issued as U.S. Pat. No. 11,009,021, which is a continuation of U.S. patent application Ser. No. 15/389,403, filed Dec. 22, 2016, now issued as U.S. Pat. No. 10,077,767, which claims the benefit under 35 U.S.C. § 119 to U.S. Provisional Patent Application Ser. No. 62/387,390, filed Dec. 24, 2015. The foregoing applications are hereby incorporated by reference into the present application in their entirety.

FIELD

The inventions disclosed herein relate generally to systems and devices for providing controlled fluid distension of the uterus in conjunction with associated medical procedures, and relates more particularly to uterine distension fluid management systems employing peristaltic pumps for use in conjunction with tissue (e.g., fibroid) removal systems.

BACKGROUND

Uterine fibroids are well-defined, non-cancerous tumors that are commonly found in the smooth muscle layer of the uterus. In many instances, uterine fibroids can grow to be several centimeters in diameter and may cause symptoms like menorrhagia (prolonged or heavy menstrual bleeding), pelvic pressure or pain, and reproductive dysfunction. Current treatments for uterine fibroids include hysteroscopic resection, which involves inserting a hysteroscope (i.e., an imaging scope) into the uterus transcervically (i.e., through the vagina), and then cutting away the fibroid from the uterus using a tissue removal device delivered to the fibroid via a channel in the hysteroscope.

Hysteroscopic resection procedures typically fall into one of two categories. In one category, an electrocautery device in the form of a loop-shaped cutting wire is fixedly mounted on the distal end of the hysteroscope, the combination of a hysteroscope and electrocautery device is referred to as a "resectoscope." Examples of resectoscope devices are disclosed, for example, in U.S. Pat. No. 5,906,615, issued May 25, 1999, which is fully incorporated herein by reference. In the other category of hysteroscopic resection procedures, an electromechanical cutter is inserted through a working channel of the hysteroscope. Tissue is then removed by contacting the end of the cutter, which typically has a rotating cutting element, with the targeted tissue attached to the uterus wall. Examples of hysteroscopic resection procedures employing an electromechanical cutter are disclosed, for example, in U.S. Pat. No. 9,095,366, issued Aug. 4, 2015, which is fully incorporated herein by reference.

In both of the above-described categories of hysteroscopic resection procedures, prior to fibroid removal, the uterus is typically distended to create a working space within the uterus. Such a working space does not normally exist in the uterus because the uterus is a flaccid organ. As such, the walls of the uterus are typically in contact with one another when in a relaxed state. The conventional technique for creating such a working space within the uterus is to administer a fluid to the uterus through the hysteroscope under sufficient pressure to cause the uterus to become distended.

By way of illustration, in the tissue removal system illustrated in FIG. 1(b) of U.S. Pat. No. 8,568,424, hereby incorporated herein by reference, distending fluid is delivered to the patient's uterus through a hysteroscope. The distending fluid is removed from the patient through three separate pathways. In particular, the distending fluid is removed from the patient (e.g., during distention and rinsing), through a removable outflow channel during a diagnostic hysteroscopy or passage of the tissue removal device, with additional fluid being lost through cervical leakage. The distending fluid that leaks through the cervix is captured in a drape and pumped to a collection container in order to account for same. The removable outflow channel is not shown in FIG. 1(b), but is described in column 16, lines 41-50 of U.S. Pat. No. 8,568,424.

Examples of the fluid used conventionally to distend the uterus include gases like carbon dioxide or, more commonly, liquids like water or certain aqueous solutions, e.g., a saline or other physiologic solution or a sugar-based or other non-physiologic solution. Because the distending fluid is administered under pressure, which may be as great as 100 mm Hg or greater, there is a risk, especially when vascular tissue is cut, that the distending fluid may be taken up by blood vessel(s) in the uterus, referred to as "intravasation," which may be harmful to the patient if too much of the distension fluid is taken up. Thus, during a procedure involving fluid distension of the uterus, it is customary to monitor the fluid uptake on a continuous basis using a scale system. Despite the risks of intravasation, with proper monitoring of fluid uptake, hysteroscopic resection is a highly effective and simple technique for removing uterine fibroids.

SUMMARY

In accordance with the exemplary disclosed embodiments, a peristaltic pumping system includes a pump console having a drive rotor that is controllably rotated by the pump console, the drive rotor comprising a roller driving feature and a roller spreader that each extend outwardly from an exterior surface of the drive rotor. A pump cartridge is detachably mounted on the drive rotor, and includes a housing and a roller assembly within the housing, the roller assembly having first and second hubs maintained in a spaced apart relationship by one or more posts extending between and defining a pump cartridge axis extending therebetween, and a plurality of planetary rollers mounted on, and extending longitudinally between, the first and second hubs, wherein the rollers are mounted in a circumferentially spaced orientation about the pump cartridge axis, each roller comprising a roller body defining a respective roller axis, wherein each roller has respective axles extending from opposite end surfaces of the roller body along the roller axis, wherein the roller axles are positioned in respective slots in, or associated with, the first and second hubs that are oriented substantially orthogonal to the roller axes so that the rollers may move in a radially outward direction away from the pump cartridge axis toward an interior wall of the housing by travel of the roller axles in the hub slots. The pump cartridge further includes a barb assembly interposed between the interior wall of the housing and an outer radially periphery of the roller assembly, the barb assembly comprising one or more compressible tubing lines. A console-mating surface of the housing and the first and second hubs collectively define a passageway through which the roller spreader extends along the pump cartridge axis, wherein angular rotation of the roller spreader relative to the roller assembly displaces the roller bodies radially outward to thereby compress contacted portions of the one or more tubing lines against the interior wall of the housing, and wherein one of a plurality of coupling features on the first hub is configured to engage the roller driving feature so that rotation of the drive rotor causes rotation of the roller assembly about the pump cartridge axis.

The coupling feature may be one of a plurality of coupling features positioned on the first hub so that the roller driving feature is engaged by the coupling feature only when the roller bodies are displaced radially outward by the spreader to compress the one or more tubing lines. In one embodiment, the coupling features are three openings in an exterior facing surfacing of the first hub spaced substantially equal-distantly apart circumferentially about the pump cartridge axis. In one embodiment, the roller driving feature is a spring-loaded detent mechanism that is at least partially depressed into the rotor by the exterior facing surface of the first hub when the pump cartridge is mounted on the console, and is fully extended once the detent mechanism engages with the respective coupling feature. In such embodiment, the pump console preferably includes one or more sensors that detect whether the detent mechanism has engaged with the coupling feature.

In various embodiments, the roller spreader comprises a plurality of radially-outwardly extending fins, each fin comprising first and second radially-outwardly extending sides that meet at an apex extending along a length of the respective fin, wherein the fin apexes are configured to engage and maintain contact with the pump cartridge roller bodies during operation of the pumping system. The roller spreader fin apexes may have flattened arcuate cross-sectional profiles for minimizing an amount of surface area contacting the respective roller bodies, and the first sides of the roller spreader fins have a curved profile configured for contacting and radially-outwardly displacing the respective roller bodies.

In one embodiment, the one or more tubing lines comprises adjacent first, second and third tubing lines arranged in a substantially parallel relationship transverse to the roller bodies, an interior surface of the pump cartridge housing comprises a first inwardly extending rib that maintains separation of the first and second tubing lines, and a second inwardly extending rib that is substantially parallel to the first rib and maintains separation of the second and third tubing lines, the plurality of rollers comprises three planetary rollers spaced substantially evenly apart circumferentially about the pump cartridge operational axis, the respective roller bodies each comprise a first circumferential groove therein to accommodate the first rib, and a second circumferential groove therein to accommodate the second rib, respectively, when the roller body is compressing the first and second tubing lines, and the roller spreader comprises three fins, respectively, wherein the respective ribs, grooves and tubing lines are all dimensioned so as to prevent the tubing lines from becoming wedged between the ribs and grooves during operation of the pumping system, and wherein the first, second and third tubing lines are fluidly connected with a single outflow fluid line (which may be one of the same three fluid lines) that is fluidly connected to an outlet port passing through the pump cartridge housing.

In accordance with another aspect of the disclosed inventions, a pump cartridge is provided for use in a peristaltic pumping system, the pump cartridge including a housing, a roller assembly within the housing, the roller assembly comprising first and second hubs maintained in a spaced apart relationship by one or more posts extending between and defining a pump cartridge axis extending therebetween, and a plurality of planetary rollers mounted on, and extending longitudinally between, the first and second hubs, wherein the rollers are mounted in a circumferentially spaced orientation about the pump cartridge axis, each roller comprising a roller body defining a respective roller axis, wherein each roller has respective axles extending from opposite end surfaces of the roller body along the roller axis, wherein the roller axles are positioned in respective slots in, or associated with, the first and second hubs that are oriented substantially orthogonal to the roller axes so that the rollers may move in a radially outward direction away from the pump cartridge axis toward an interior wall of the housing by travel of the roller axles in the hub slots, and a barb assembly interposed between the interior wall of the housing and an outer radially periphery of the roller assembly, the barb assembly comprising one or more compressible tubing lines. A console-mating surface of the housing and the first and second hubs collectively define a passageway to accommodate a roller spreader inserted along the pump cartridge axis and rotated relative to the roller assembly to displace the roller bodies radially outward and thereby compress contacted portions of the one or more tubing lines against the interior wall of the housing, wherein the roller assembly may be rotated relative to the roller spreader so that the roller spreader displaces the roller bodies radially outward to thereby compress contacted portions of the one or more tubing lines against the interior wall of the housing, and wherein one of a plurality of coupling features on the first hub is configured to engage a roller driving feature of a pump console so that rotation of the engaged driving feature would causes rotation of the roller assembly about the pump cartridge axis.

The coupling feature may be one of a plurality of coupling features positioned on the first hub so that the roller driving feature is engaged by the coupling feature only when the roller bodies are displaced radially outward by the spreader to compress the one or more tubing lines. For example, in one embodiment, the plurality of coupling features consists of three openings in an exterior facing surfacing of the first hub spaced substantially equal-distantly apart circumferentially about the pump cartridge axis, and the roller driving feature comprises a spring-loaded detent mechanism that is at least partially depressed into the rotor by the exterior facing surface of the first hub when the pump cartridge is mounted on the console, and is fully extended once the detent mechanism engages with the respective coupling feature.

In one embodiment of the pump cartridge, the one or more tubing lines comprises adjacent first, second and third tubing lines arranged in a substantially parallel relationship transverse to the roller bodies, an interior surface of the pump cartridge housing comprises a first inwardly extending rib that maintains separation of the first and second tubing lines, and a second inwardly extending rib that is substantially parallel to the first rib and maintains separation of the second and third tubing lines, the plurality of rollers comprises three planetary rollers spaced substantially evenly apart circumferentially about the pump cartridge operational axis, and the respective roller bodies each comprise a first circumferential groove therein to accommodate the first rib, and a second circumferential groove therein to accommodate the second rib, respectively, when the roller body is compressing the first and second tubing lines, wherein the respective ribs, grooves and tubing lines are all dimensioned so as to prevent the tubing lines from becoming wedged between the ribs and grooves during operation of the pump cartridge. The first, second and third tubing lines are preferably fluidly connected with a single outflow fluid line (which may be one of the first, second or third tubing lines) that is fluidly connected to an outlet port passing through the pump cartridge housing.

Other and further embodiments, as well as aspects, features and advantages, of the disclosed inventions are set forth in part in the detailed description which follows, and in part will be inherent or otherwise obvious from the description or may be learned by practice of the disclosed embodiments.

In the following detailed description, reference is made to the accompanying drawings which form a part thereof and in which is shown by way of illustration various embodiments for practicing the disclosed inventions. The embodiments are described in sufficient detail to enable those skilled in the art to practice the disclosed inventions, and it is to be understood that other embodiments may be utilized, and that structural changes may be made to the described embodiments, without departing from the scope of the disclosed inventions. The following detailed description is, therefore, not to be taken in a limiting sense, and the scope of the disclosed inventions is to be defined solely by the appended claims and their legal equivalents.

BRIEF DESCRIPTION OF THE DRAWINGS

The above and other aspects and features of the disclosed embodiments will become more apparent upon consideration of the ensuing detailed description, taken in conjunction with the accompanying drawings, in which like reference characters refer to like parts throughout, and in which:

FIGS. 2A, 2B and 2C are perspective, rear and exploded views, respectively, of an embodiment of an outflow pump cartridge configured for use with the console shown in FIG. 1;

FIGS. 4A and 4B are perspective and rear views of a barb assembly used in the outflow pump cartridge shown in FIGS. 2A-2C;

FIG. 4C is a cross-sectional view of the barb assembly taken along line 4C in FIG. 4B;

FIG. 7B is a cross-sectional view of the external housing and roller assembly of the outflow pump cartridge taken along line 7B in FIG. 7A;

FIGS. 7C and 7D are cut-away side views of the external housing and the roller assembly of the outflow pump cartridge;

FIGS. 10A and 10B are perspective and front views, respectively, of another embodiment of a drive rotor shaft upon which the inflow or outflow pump cartridge is mounted during operation;

FIG. 11 is a perspective view of a drive rotor socket located on the console of FIG. 1, including the drive rotor shaft shown in FIGS. 10A and 10B, which may be used for mounting the inflow or outflow pump cartridge;

DETAILED DESCRIPTION OF THE ILLUSTRATED EMBODIMENTS

The disclosure is described below primarily in the context of devices and systems optimized for fluid management in one or more therapeutic or diagnostic gynecological or urological procedures such as the removal of uterine polyps or fibroids. However, the devices and systems of the disclosure may be used in a wide variety of applications. For example, the devices disclosed herein can be optimized for use in any system where fluid is pumped into the patient through an input line, and fluid is pumped out through one or more output lines. Thus, it should be understood by one of ordinary skill in the art that, although one of the exemplary embodiments described herein is directed to a fluid management system having three fluid lines in the outflow, the fluid management system is not so limited and may be equipped to have two, three, or more fluid lines in the outflow of the system to which it is coupled.

Figure 1:
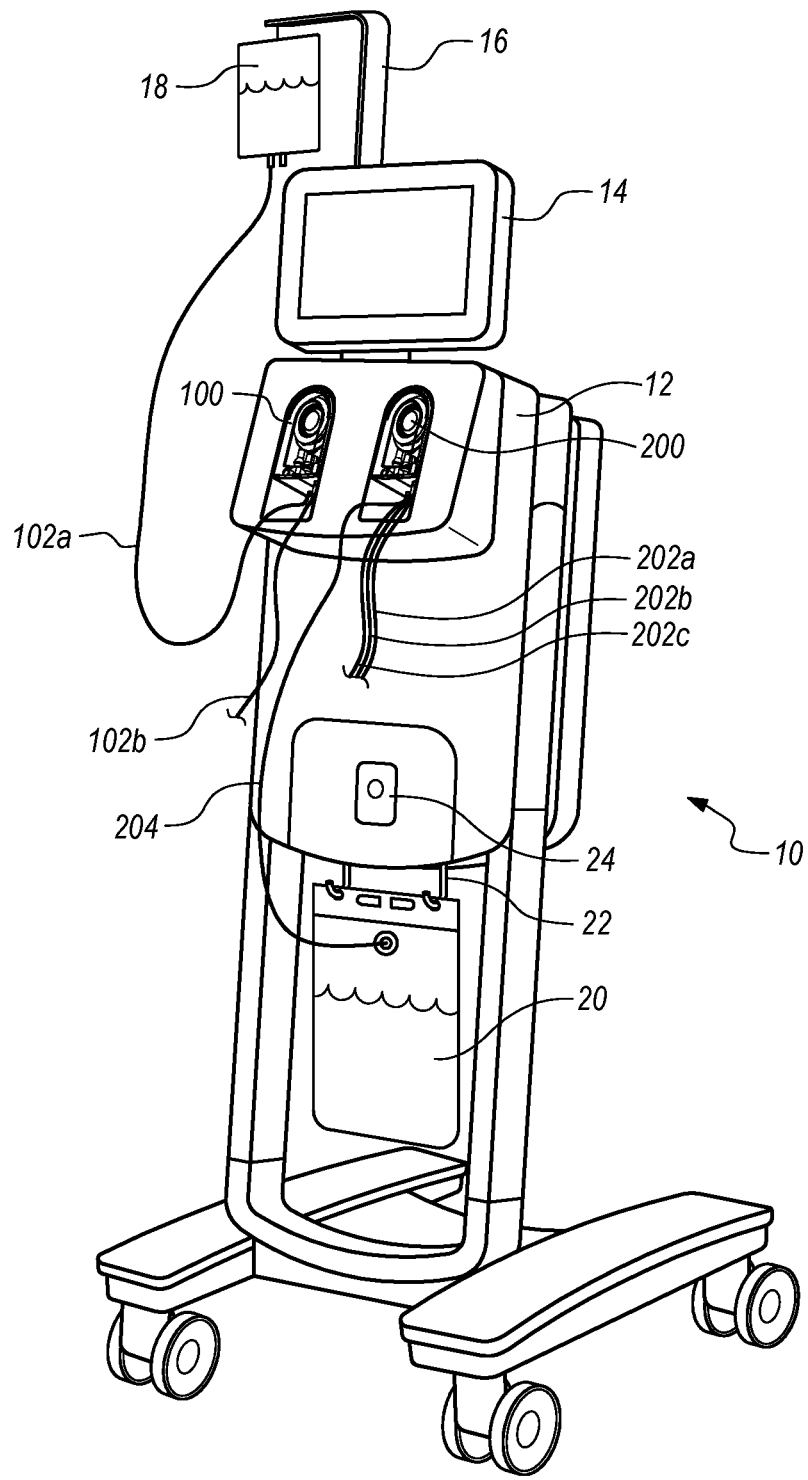
FIG. 1 is a perspective view of an exemplary fluid management system, including a peristaltic pump console and associated equipment.

An exemplary system 10 for providing controlled uterine distension fluid management in conjunction with a hysteroscopic resection (uterine tissue removal) procedure is shown in FIG. 1. The system 10 includes a cart 12 on which an inflow pump cartridge 100 and an outflow pump cartridge 200 are mounted. Respective inflow and outflow pump motors (not shown) are housed within the cart 12. A monitor 14 coupled to the cart 12 may be used to input and display system settings. The system 10 further includes a pole 16 upon which a fluid bag 18 containing a source fluid may be mounted. The lower portion of the cart 12 includes hooks 22 for holding a waste fluid bag 20. The lower portion of the cart 12 further includes a connection receptacle 24 for connection to a tissue removal system, such as that disclosed in the above-incorporated U.S. Pat. No. 8,568,424.

The cart 12, pump motors, monitor 14, pole 16, waste fluid bag holder 22, and rotor shafts (not visible in FIG. 1) upon which the cartridges 100 and 200 are mounted are part of the capital equipment of the system 10. In this manner, the capital equipment is not exposed to the fluid, and thus the cleanliness of the capital equipment may be maintained. As such, the capital equipment can be used in many procedures on many different patients before being replaced. Conversely, because they contact the fluid and are thus internally contaminated during the procedure, the inflow and outflow pump cartridges 100 and 200 are intended to only be used in a single procedure performed on a single patient.

Figure 1A:
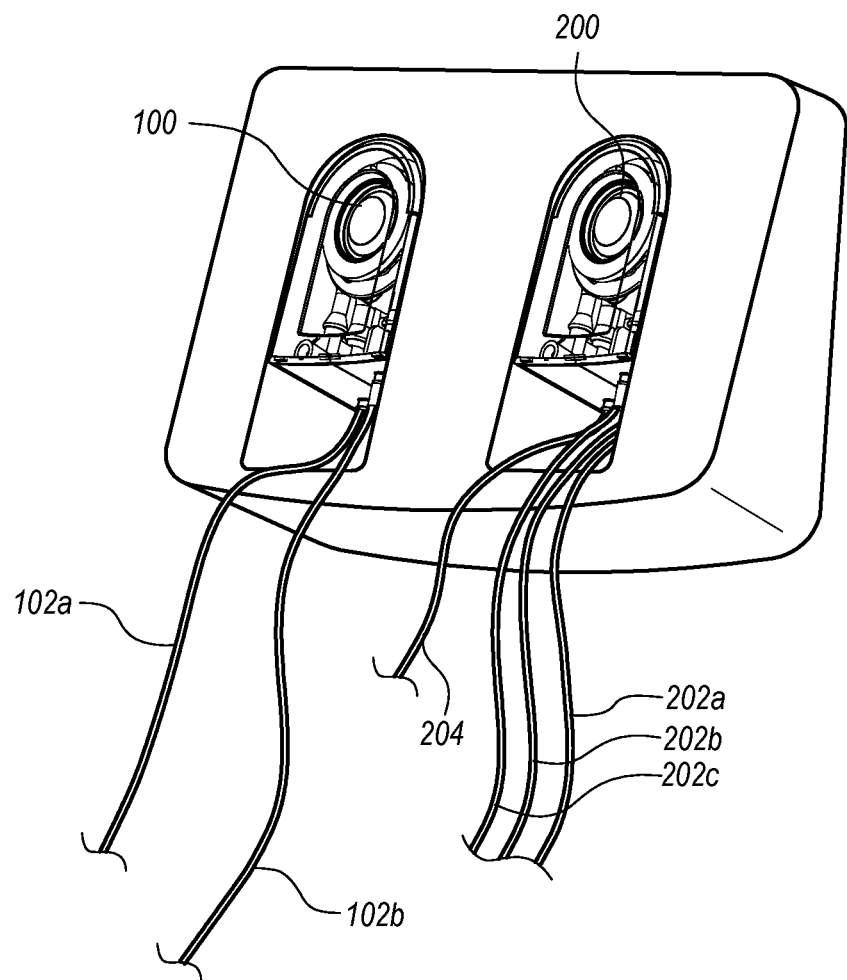
FIG. 1A is a perspective view of a portion of the peristaltic pump console of FIG. 1, including respective fluid inflow and outflow pump cartridges mounted thereon.

The inflow and outflow pump cartridges 100 and 200 mounted on the cart 12 are shown in greater detail in FIG. 1A. The inflow pump cartridge 100 is coupled to a fluid tube having two portions, 102a and 102b. A first portion of the fluid tube, 102a, is carrying fluid flowing into the inflow pump cartridge 100 from a fluid source, such as a saline bag 18. The other fluid tube portion, 102b, is carrying fluid flowing out of the inflow pump cartridge 100 to the patient. The outflow pump cartridge 200 is coupled to three incoming fluid tubes, 202a, 202b, and 202c, located on one side of the outflow pump cartridge 200, and to a single outgoing fluid tube 204 located on the other side of the outflow pump cartridge 200. The three incoming fluid tubes 202a, 202b, and 202c carry fluid flowing from respective components of the tissue removal system, which are combined within the outflow pump cartridge 200 and discharged through the single outgoing fluid tube 204.

For example, when the fluid management system 10 is coupled to a tissue removal system, such as that described in the above-incorporated U.S. Pat. No. 8,568,424, the outflow pump cartridge 200 may be coupled to (i.e., and receive fluid from) each of a tissue removal device, a removable outflow channel, and a buttocks drape that collects fluid that leaks from the cervix of the patient during the procedure. However, it should be understood that alternate embodiments of the outflow pump cartridge 200 may be configured for receiving less than or more than three incoming fluid lines, as will be apparent to those of ordinary skill in the art. The outgoing fluid tube 204 is coupled to the fluid waste bag 20. The fluid waste bag 20 may be coupled to a scale (not shown) for monitoring the amount of fluid that is removed from the tissue removal system. As discussed above, continuous monitoring of fluid uptake reduces the risk of fluid overload.

Figure 2A:
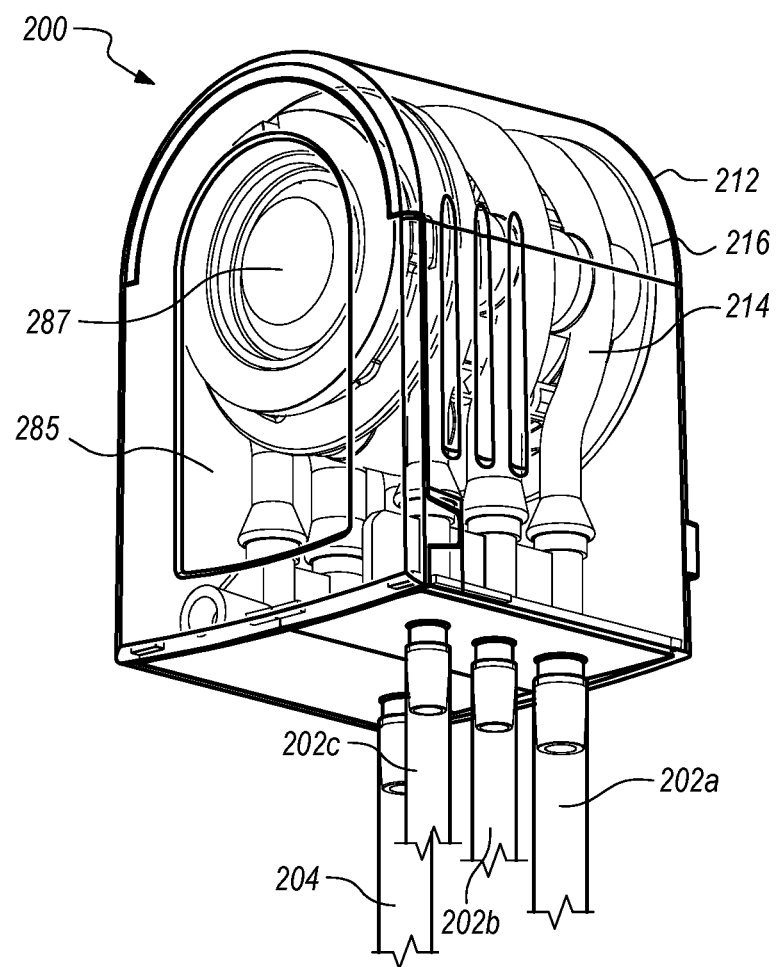
Figure 5A:
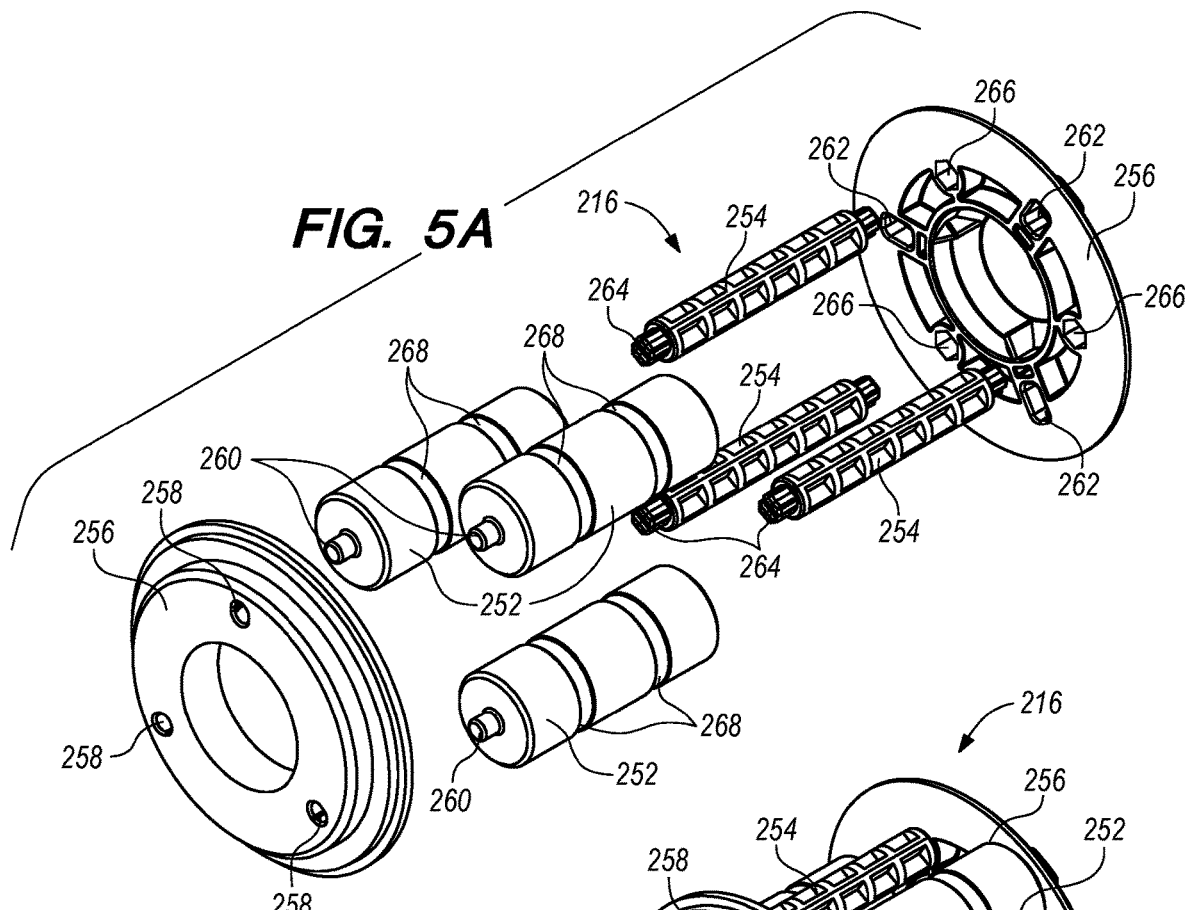
FIGS. 5A and 5B are exploded and perspective views, respectively, of a roller assembly used in the outflow pump cartridge shown in FIGS. 2A-2C.
Figure 5B:
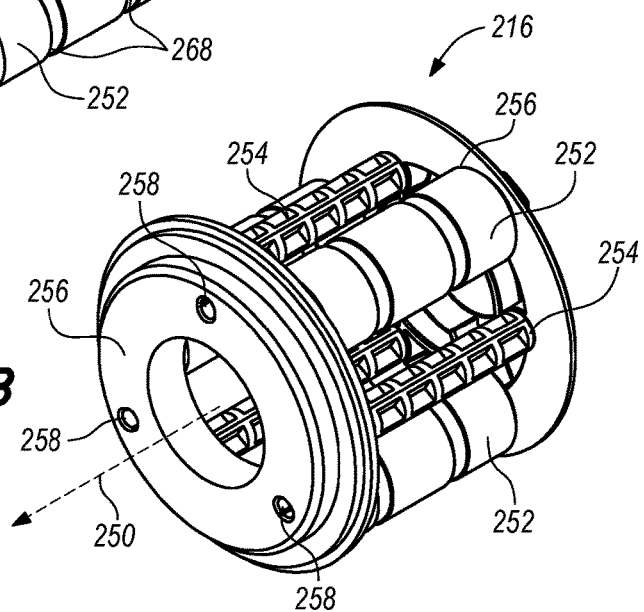
Figure 5C:
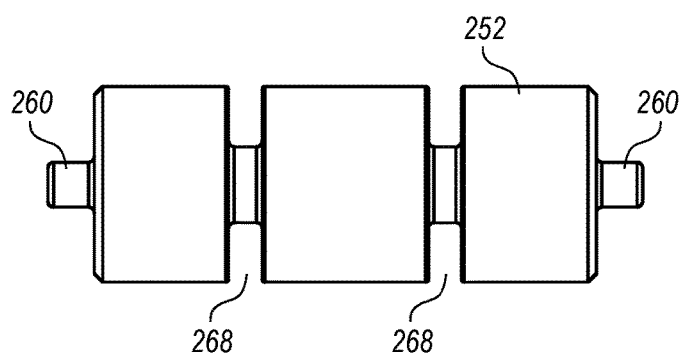
FIG. 5C is a side view of an exemplary roller body of the roller assembly shown in FIGS. 5A and 5B.

With reference to FIGS. 2A-2C, the outflow pump cartridge 200 includes a pump cartridge housing 212 (shown separately in FIGS. 3A and 3B), a barb assembly 214 (shown separately in FIGS. 4A-4C), and a roller assembly 216 (shown separately in FIGS. 5A-5C). The front of the housing, seen in FIG. 2A, includes a see-through panel 285 (essentially a molding artifact) through which a circular bottom piece 287 of the roller assembly 216 is visible. The rear of the housing 212, shown in FIG. 2B, includes an opening 240 for accommodating passage therethrough of a pump drive rotor 300 (shown in phantom in FIG. 2B) extending from the console 12. As described in greater detail below, the pump drive rotor 300 includes a central cylindrical rotor shaft 304 with three fins 306 protruding radially outwardly from the shaft 304.

As shown in FIG. 2C, the housing 212 includes a spacer ring 212a for accommodating the roller assembly 216, and a front face plate 212b. The outflow pump cartridge 200 also includes a ferromagnetic disc 222 that fits within an opening 224 in rear face of the housing 212 (i.e., the face that mates against the console rotor) and interfaces with an electromagnet coupled to the pump console cart 12, as discussed in greater detail below. In order to mimic the design of the inflow pump cartridge 100 (which is discussed in greater detail below), the rear face of the housing 212 includes a indented circular portion 226 that is in a same place as the pressure sensor assembly 123, 120 mounted in the rear face of the inflow cartridge 100 and described below in conjunction with FIG. 9B.

Figure 3A:
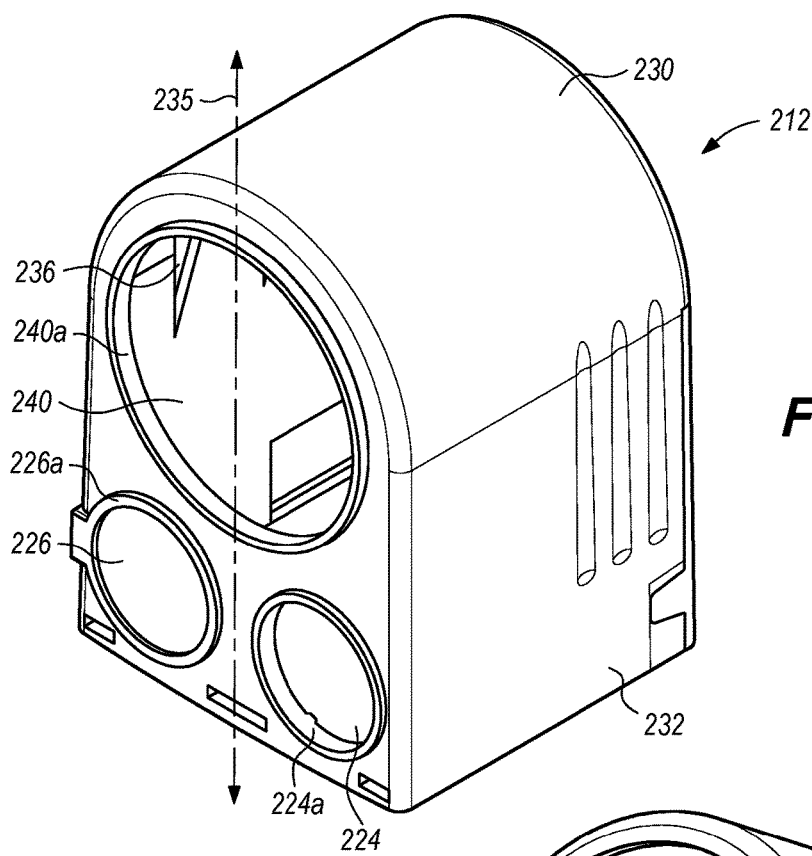
FIGS. 3A and 3B are perspective views of an ornamental external housing for the outflow pump cartridge shown in FIGS. 2A-2C.
Figure 3B:
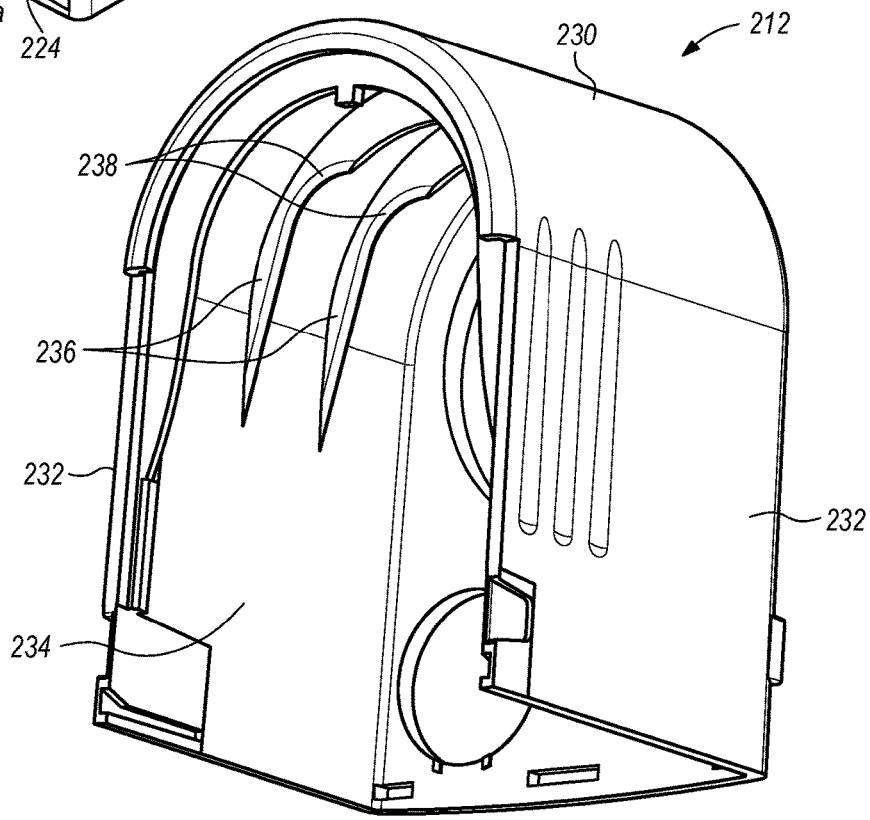

With reference to FIGS. 3A and 3B, the exterior of the outflow cartridge housing 212 has an ornamental design that may be generally characterized as arc-shaped, with a rounded top 230, parallel sides 232, and a flat bottom. The interior wall 234 of the housing 212 includes a pair of ribs 236 protruding inwardly therefrom. As discussed below, the ribs 236 limit the extent to which flexible tubing 242a, 242b and 242c of the barb assembly 214 can slide longitudinally along the rollers 252 of the roller assembly 216. The ribs 236 include circular cutouts 238 to accommodate the rollers 252 during assembly, as is discussed below in greater detail. The shape of the cutouts 238 mimics the shape of the outer surface of the rollers 252. The openings 240 and 224, and feature 226 in the rear face of the housing 212 include rims 240a, 224a, and 226a, respectively, protruding therefrom. The protruding rims 240a, 224a and 226a are approximately the same depth all the way around and the same depth as each other. In this manner, the rims 240a, 224a and 226a are the only surfaces on the rear face of the housing 212 that are in contact with the pump console cart 12 when the cartridge 200 is mounted thereon, and the rims 240a, 224a and 226a hold the outflow pump cartridge 200 stable against the drive rotor during operation.

The barb assembly 214, shown separately in FIGS. 4A, 4B, and 4C, includes three flexible, fluid carrying tubes ("fluid tubes" or "fluid lines") 242a, 242b and 242c, each of which is connected to a respective external inflow barb 244a, 244b, 244c on one end. At the other end, all three fluid tubes 242a, 242b, and 242c, are fluidly coupled to a single external outflow barb 246. As shown in FIG. 4C, the outflow end of two of the fluid tubes, 242a and 242b, terminates in a horizontal channel 248, which channel 248 is coupled to the external outflow barb 246. In this manner, the outflow pump cartridge 200 may accommodate the three separate incoming fluid lines 202a, 202b, and 202c, connected to the outflow pump cartridge 200. Alternatively, the barb assembly may have less than or more than three fluid lines, depending on the number of incoming fluid lines that are connected to the outflow pump cartridge 200. The barb assembly 214 further includes a plate 247 for supporting the ferromagnetic disc 222 and maintaining the position of the ferromagnetic disc 222 within the opening 224 in the housing 212.

The roller assembly 216, shown in greater detail in FIGS. 5A, 5B, and 5C, has a primary axis 250 extending through the center of the roller assembly 216. Three planetary rollers 252 are freely rotatable about the primary axis 250, and are mounted in spaced relation to the primary axis 250, and to each other. The rollers 252 are circumferentially spaced about the roller assembly 216, and are equally spaced from the primary axis 250. The rollers 252 are cylindrical with axle-like protrusions 260 extending axially from each end. Each of the rollers 252 includes two grooves 268 for accommodating the ribs 236 in the housing 212 when the roller assembly 216 is positioned within the housing 212, as discussed below in greater detail. Three posts 254 are mounted between the rollers 252. The posts 254 are cylindrical with protrusions 264 on each end. The roller assembly 216 further includes front and rear disc-shaped hubs 256. Each of the ends of the rollers 252 and posts 254 are coupled to hubs 256. The protrusions 260 on the ends of the rollers 252 are seated in elongated channels 262 in the inner surface of the hubs 256. The protrusions 260 and channels 262 have dimensions that allow the rollers 252 to rotate about their axes and move radially relative to the hubs 256. The protrusions 264 on the posts 254 are inserted into openings 266 in the inner surface of the hubs 256. The outer surfaces of the hubs 256 include openings 258, which are configured to engage with a pin 314 protruding from a rotor 300 (shown in FIGS. 8A and 8B) during operation, such that the pin 314 drives the rotation of the roller assembly 216 about its axis 250, as discussed in greater detail below.

Figure 6:
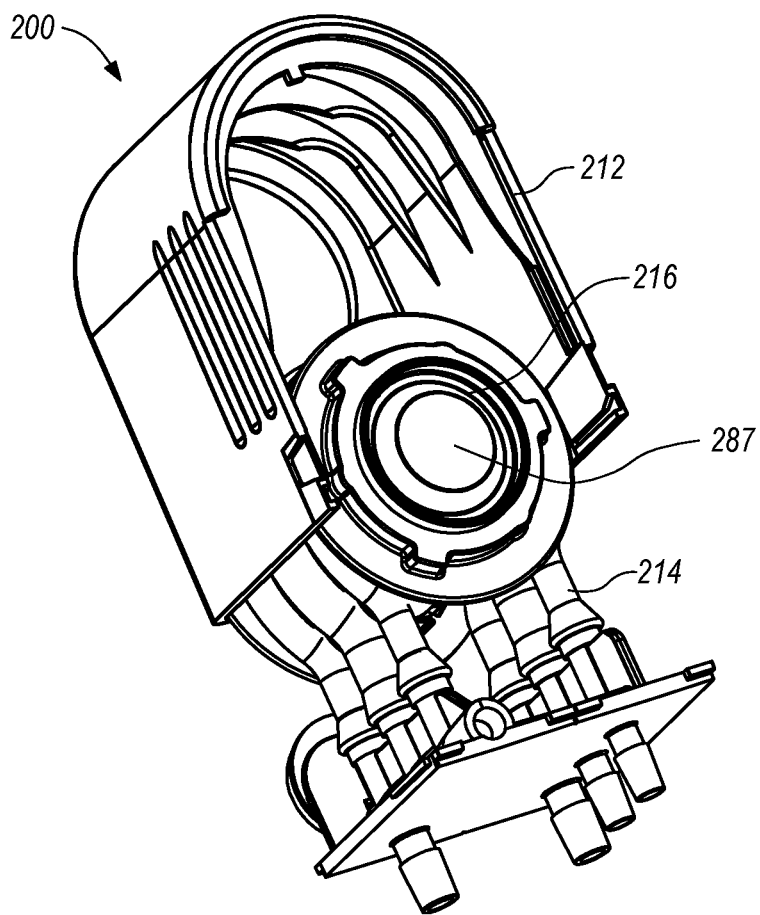
FIGS. 6 and 7A are perspective views of the outflow pump cartridge components during assembly.
Figure 7A:
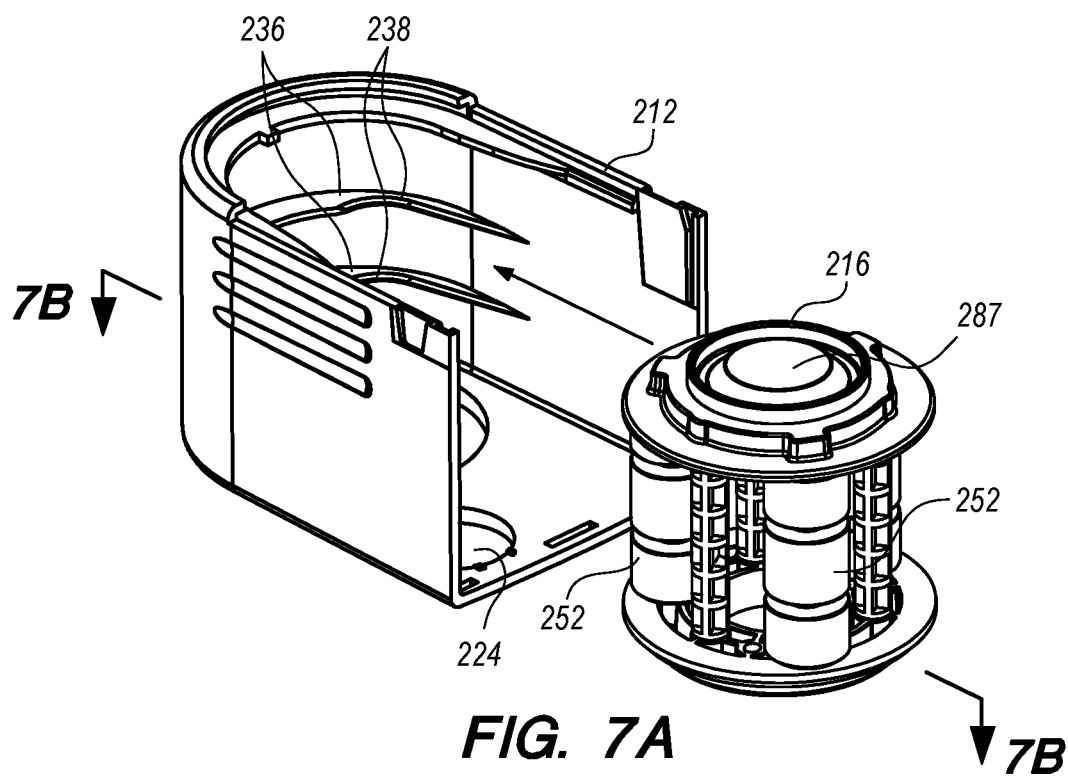

In order to assemble the outflow cartridge 200, the roller assembly 216 is positioned within the barb assembly 214, such that the fluid lines 242a, 242b, and 242c surround the rollers 252, as shown in FIG. 6. Together, the roller assembly 216 and barb assembly 214 are slid into the housing 212. Further details regarding the assembly of the outflow cartridge 200 are shown in FIGS. 7A through 7D, in which the barb assembly 214 has been removed to more clearly show how the housing 212 accommodates the roller assembly 216. As shown in FIG. 7A, the roller assembly 216 is slid into the housing 212 with the rollers 252 positioned to align with the circular cutouts 238 in the ribs 236 of the housing 212. In this manner, as shown in FIGS. 7B and 7C, when the roller assembly 216 is initially positioned within the housing 212, the ribs 236 do not interfere with the roller assembly 216 when two of the rollers 252 are positioned at 10:00 and 2:00. Conversely, if the rollers 252 are not properly positioned before the roller assembly 216 slides into the housing 212, the ribs 236 in the housing 212 will interfere with the rollers 252, preventing proper positioning of the roller assembly 216. That is, if the rollers 252 are not positioned in alignment with the cutouts 238, then the rollers 252 will come into contact with the ribs 236 before the roller assembly 216 is able to slide completely into the housing 212.

After sliding the roller assembly 216 into the housing 212 in the correct position, the roller assembly 216 then moves relative to the housing 212 and towards the opening 240 in the housing 212, so that a portion of one of the hubs 256 of the roller assembly 216 is seated within the opening 240 in the housing 212, as shown in FIG. 7D. When the roller assembly 216 is seated within the housing 212 as shown in FIG. 7D, the grooves 268 on the rollers 252 accommodate the ribs 236 in the housing 212. As the roller assembly 216 rotates, the ribs 236 of the housing 212 may protrude into the grooves 268 on the rollers 252. When the outflow pump cartridge 200 is properly assembled, the ribs 236 in the housing 212 prevent the tubes 242a, 242b, and 242c of the barb assembly 214 from moving longitudinally along the rollers 252 and becoming disposed within grooves 268. The front tube 242a of the barb assembly 214 is positioned between the front hub 256 of the roller assembly 216 and the front rib 236 of the housing 212, the middle tube 242b of the barb assembly 214 is positioned between the two ribs 236 of the housing 212, and the rear tube 242c of the barb assembly 214 is positioned between the rear rib 236 and the rear hub 256 of the roller assembly 216.

In an alternate embodiment (not shown), the housing 212 may comprise two pieces that are coupled together with a hinge along the top of the housing 212 about which the two pieces may rotate, so that the housing 212 may open up along the longitudinal axis (shown as dashed line 235 in FIG. 3A). The barb assembly 214 with the roller assembly 216 disposed therein may be positioned between the two pieces of the housing in the open position and then the two pieces may be rotated towards each other and closed around the barb assembly 214 and roller assembly 216. In this alternate embodiment, the circular cutouts 238 in the ribs 236 of the housing 212 may be unnecessary.

Figure 8A:
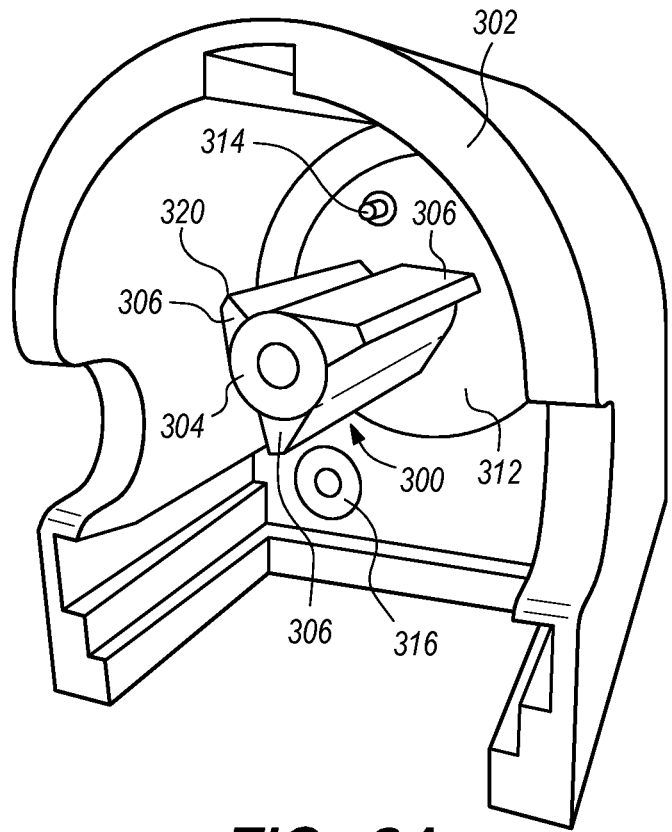
FIGS. 8A and 8B are perspective and front views, respectively, of one embodiment of a drive rotor socket and drive rotor located on the console of FIG. 1, upon which the outflow pump cartridge is mounted during operation.
Figure 8B:
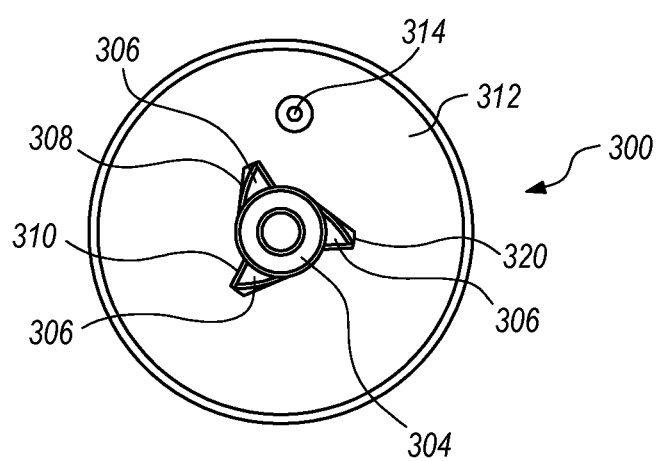

During operation, the outflow pump cartridge 200 is removably mounted on a rotor 300, such as the one depicted in FIGS. 8A and 8B. In particular, the rotor 300 is coupled to a drive motor housed within the cart 12 shown in FIG. 1. The rotor 300 is disposed within an arc-shaped rotor housing 302, which is dimensioned for accommodating the outflow pump cartridge 200 therein. The rotor 300 includes a roller spreader comprising a central cylindrical shaft 304 and three fins 306 protruding radially from the shaft 304. The roller spreader fins 306 are generally triangular in cross-section, with each fin 306 having first and second radially-outwardly extending sides, 308 and 310, that meet at an apex 320 extending along a length of the respective fin 306 and configured to engage and maintain contact with the pump cartridge rollers 252 during operation of the pumping system. The roller spreader fin apexes 320 preferably have a flattened arcuate cross-sectional profile for minimizing an amount of surface area contacting the rollers and thereby reduce frictional resistance to rotation of the roller assembly during operation of the pumping system. The respective first surfaces 308 of the roller spreader fins 306 preferably have a curved profile extending radially outward from the central cylindrical shaft 304 for contacting and displacing the rollers 252 when the rotor 300 is rotated in a counter-clockwise direction relative to the pump cartridge 200 from the perspective of the system operator, with the second sides 310 of the fins being generally flat and extending generally tangential to the shaft 304.

The cylindrical shaft 304 is coupled to a circular rotating rear surface 312 that also includes a spring-loaded protruding pin 314. The pin 314 is biased to be in an outward protruding position, as shown in FIG. 8A. An electromagnet 316 disposed within the rotor housing 302 interfaces with the ferromagnetic disc 222 in the cartridge housing 212 to retain the outflow pump cartridge 200 on the shaft 304. The force between the electromagnet 316 and the ferromagnetic disc 222 is strong enough to prevent the cartridge 200 from being inadvertently dislodged from the cart 12.

When the outflow pump cartridge 200 is initially mounted on the rotor 300, the fins 306 are disposed in the spaces between the rollers 252, as shown in phantom in FIG. 2B. In this initial position, the rear exterior surface of outflow pump cartridge 200 pushes on the spring-loaded pin 314 and forces it into a compressed position, which is sensed by a sensor within the console (described in greater detail below in conjunction with FIG. 26). When the rotor 300 is initially activated, the rotor 300 rotates relative to the rollers 252 until the fins 306 on the rotor shaft 300 engage the rollers 252. While friction substantially prevents the roller assembly from rotating, the fins 306 push the rollers 252 radially outward, away from the primary axis 250 of the roller assembly 216. The radial outward motion of the rollers 252 is indicated by arrows 318 and the clock-wise rotational movement of the rotor shaft 304 is indicated by arrow 340 in FIG. 2B. In this manner, rotation of the rotor 300 relative to the roller assembly 216 causes the respective curves surfaces 308 of the spreader fins to engage and displace the respective rollers 252 radially outwardly until the rollers are riding on the fin apexes 320.

In particular, the rotor 300 continues to rotate relative to the roller assembly 216 until the spring-loaded drive pin 314 is aligned with one of the openings 258 in the outer surface of the hub 256 of the roller assembly 216, at which point the pressure from the roller assembly 216 that compresses the drive pin 314 is removed and the pin 314 automatically protrudes into the opening 258, which event is sensed by the sensor assembly in the console 12, as described below. Once the drive pin 314 protrudes into the opening 258, further circumferential movement of the pin 314 about axis 250 of the rotor 300 drives rotation of the roller assembly 216 relative to cartridge housing 230. In particular, once the rollers 252 are in the radially expanded position and the drive pin 314 protrudes into the opening 258, the rollers 252 and the rotor 300 rotate circumferentially in unison about the rotor axis. Rotation of the rotor shaft 300 causes the roller assembly 216 to rotate about its primary axis 250 as rollers 252 rotate on their own axes while being maintained in the radially outward position by the respective fin apexes 320, as explained in greater detail below.

In order to prevent inadvertent twisting of the roller assembly 216 by the drive pin 314 (due to the rotating force being entirely imparted on the front hub, a plurality of engaging teeth 253 are integrally molded into the end cap 287 of the roller assembly 216 (best seen in FIG. 9A). the teeth 253 are engaged by the axial ends of the respective roller spreader fins 306, so that the rotational force applied by the rotor 300 is applied on both ends of the roller assembly. Notably, the teeth 253 are configured to engage and be rotated (e.g., like a socket wrench) when the shaft 304 is rotated in the counter-clockwise direction (from the perspective of the system operator). This allows the same manufacturing process to be used for both the outflow and inflow roller assemblies 216 and 116, since the inflow assembly may be rotated clockwise (in which case the teeth 253 are not engaged), although (as explained below) this would not normally be the case for the outflow assembly.

Notably, each roller 252 rotates about its own axis during operation such that the outer surface of the roller rubs against the respective fin apex 320. The flattened arcuate cross-sectional profile shape of the apex 320 minimizes friction between the rollers 252 and the fins 306. In the radially expanded position, the rollers 252 engage and compress the tubing 242a, 242b, and 242c that extends around the roller assembly 216 so that sections of the tubing 242a, 242b, and 242c are flattened between the outside of the roller 252 and the interior wall of the housing 212. As the shaft 300 turns, the rollers 252 move along the tubes 242a, 242b, and 242c and produce a peristaltic type pumping action along the tubes 242a, 242b, and 242c.

Figure 26:
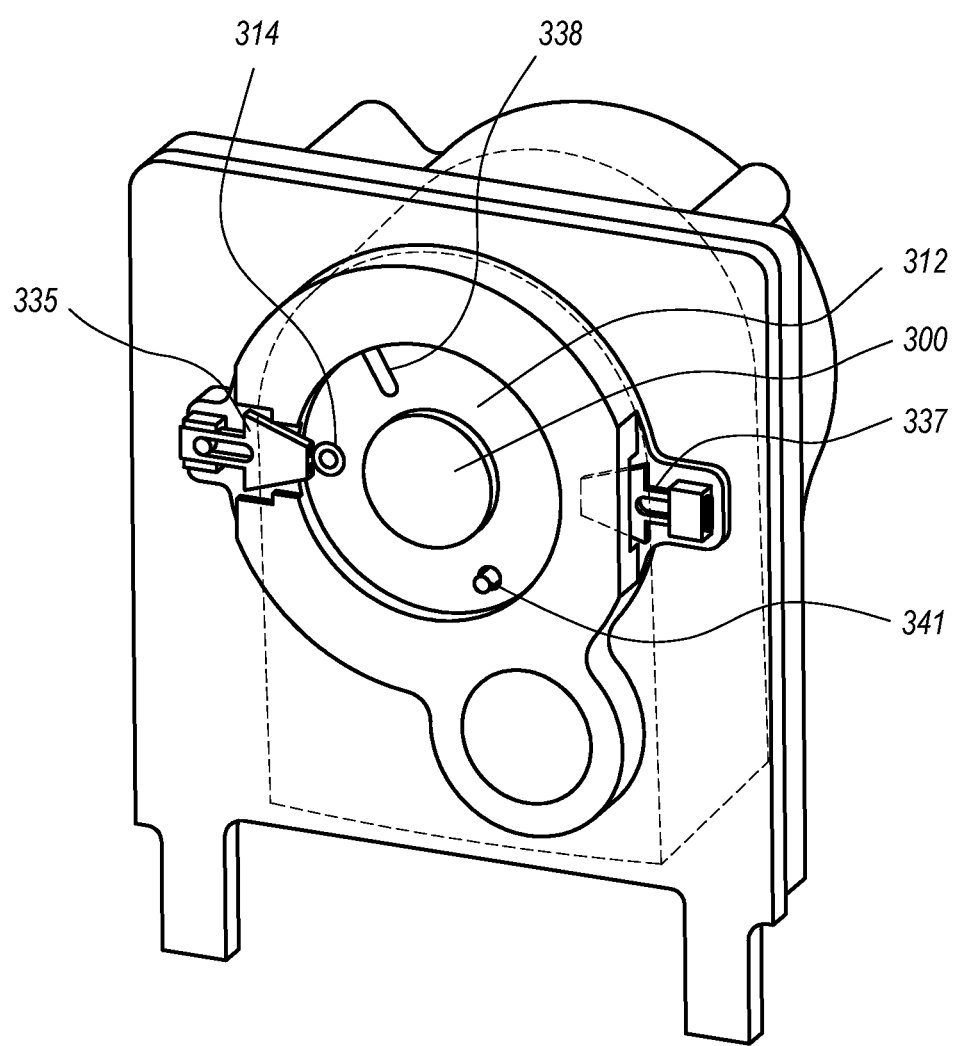
FIG. 26 is a perspective view of an interior wall of the console underlying the drive rotor socket for one of the inflow or outflow pump cartridges, including a sensor that senses whether a spring loaded pin protruding from the drive rotor socket is fully extended or otherwise at least partially depressed.

With reference also to FIG. 26, an optical sensor 335 is mounted on an interior wall of the cart 12 underlying the rotor 300, and is configured to detect whether the drive pin 314 is at least partially depressed into the rotor. An additional sensor (not shown) also detects whether a pump cartridge has been mounted on the respective rotor, and between these two sensors it can be confirmed when a pump cartridge has been mounted, and thereafter whether the drive pin has engaged with a coupling feature on the respective pump cartridge. In addition, a further sensor 337 is included to detect rotation of the rotor 300 by detecting when a groove or slot 338 cut into the rotor 300 passes the sensor 337. The output of this sensor can be compared to an expected point in time that the slot will be detected based on the rotor rotational speed, and if the detected time does not align with the projected time, an error message may be delivered and pump operation may be stopped. Further seen in FIG. 26 is an added pin 341 that can be used for this same purpose using the sensor 335.

The design of the respective rotor 300 and outflow pump cartridge 200 prevents them from operating in the reverse direction. In particular, due to the shape of the fins 306 on the rotor 300, operating the rotor 300 in the reverse direction will not cause the roller assembly 216 to rotate in the opposite direction. When the rotor shaft 300 rotates in a counter-clockwise direction, the curved portion 308 of the fins 306 will push the rollers 252 radially outward, and then when the rollers 252 encounter the straight portion 310 of the fin 306, the rollers 252 will automatically move radially inward due to the pressure applied on the rollers 252 by the tubes 242, particularly if occupied by fluid. Alternatively, the rotor 300 may be coupled to a motor that is not reversible. Regardless, the outflow pump is preferably not reversible so that tissue removed by the tissue removal system is prevented from being pumped back in to the tissue removal system.

Figure 9A:
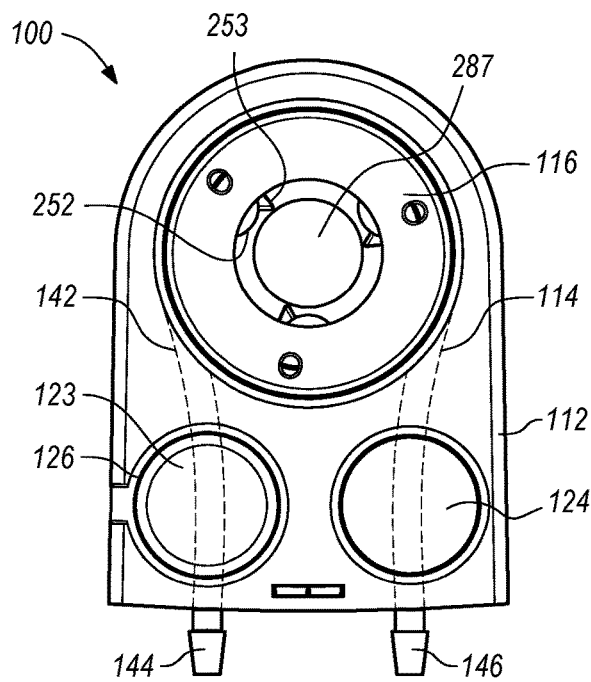
FIGS. 9A and 9B are rear and exploded views, respectively, of an inflow pump cartridge for the fluid management system shown in FIG. 1.
Figure 9B:
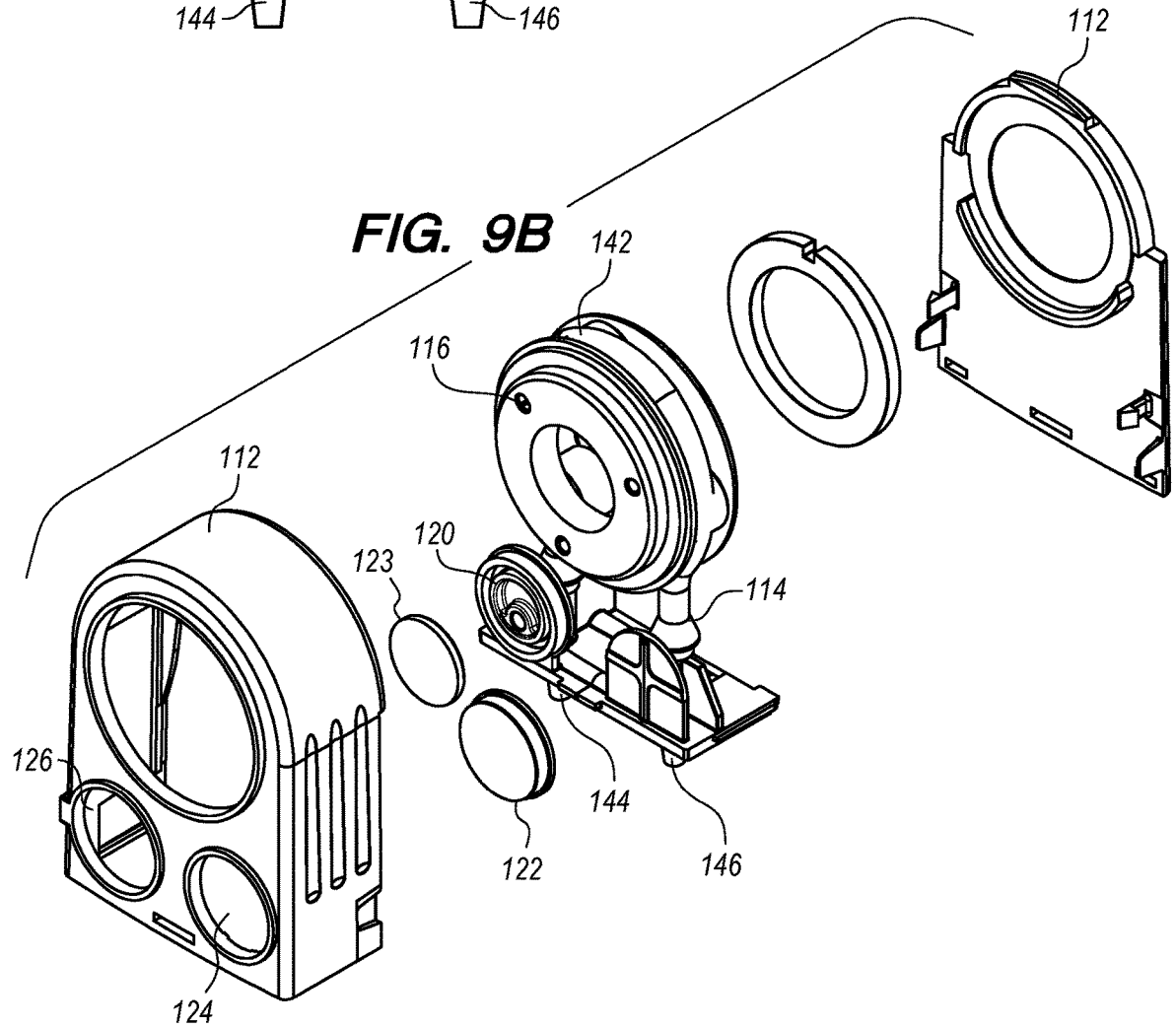
Figure 12:
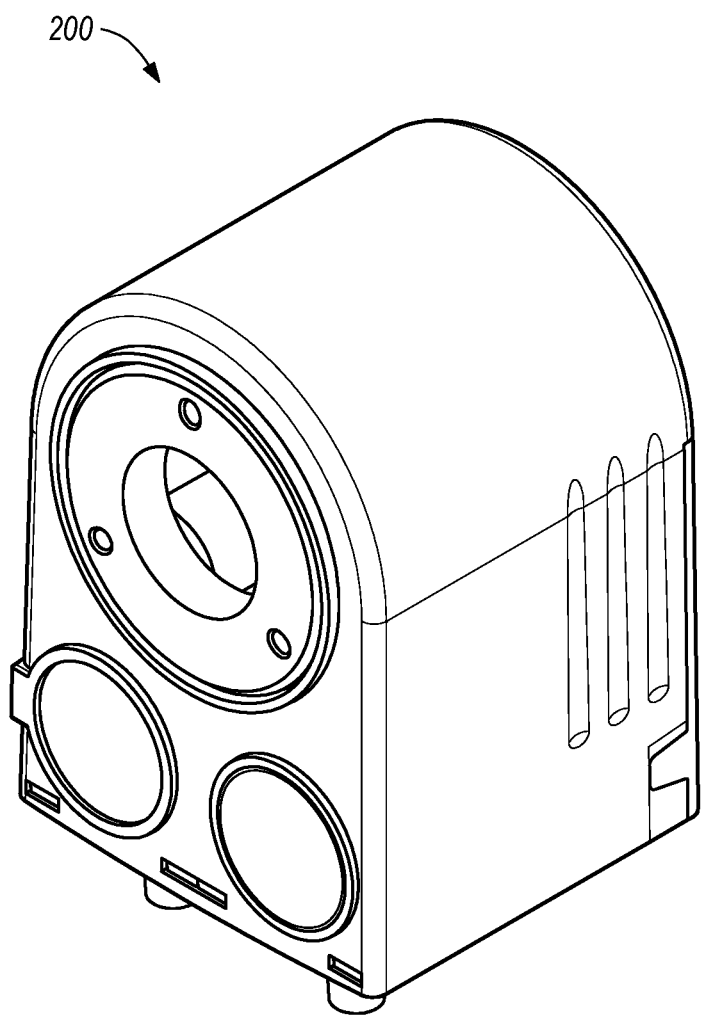
FIGS. 12-25 are various perspective, side, bottom, top, and cut-away views of the ornamental housings of the respective outflow and inflow pump cartridges.
Figure 13:
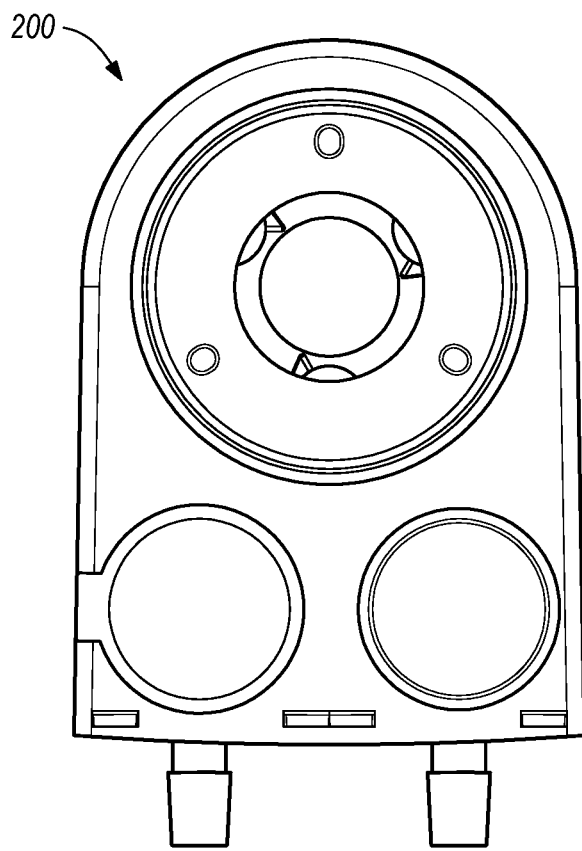
Figure 14:
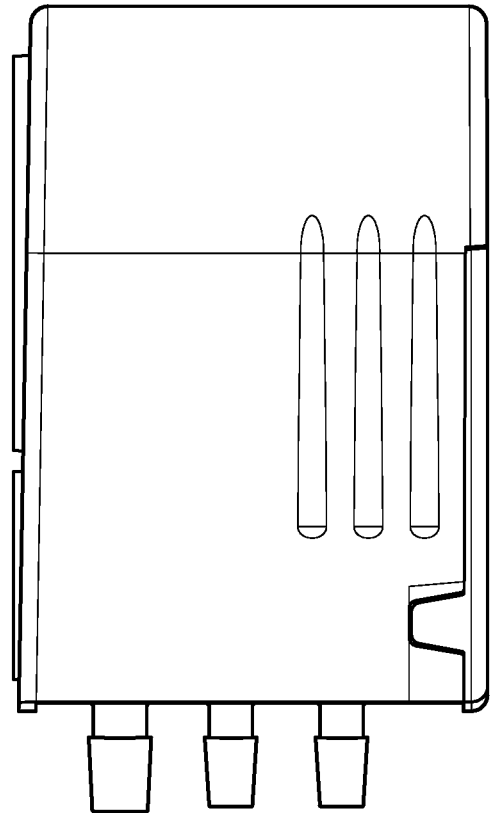
Figure 15:
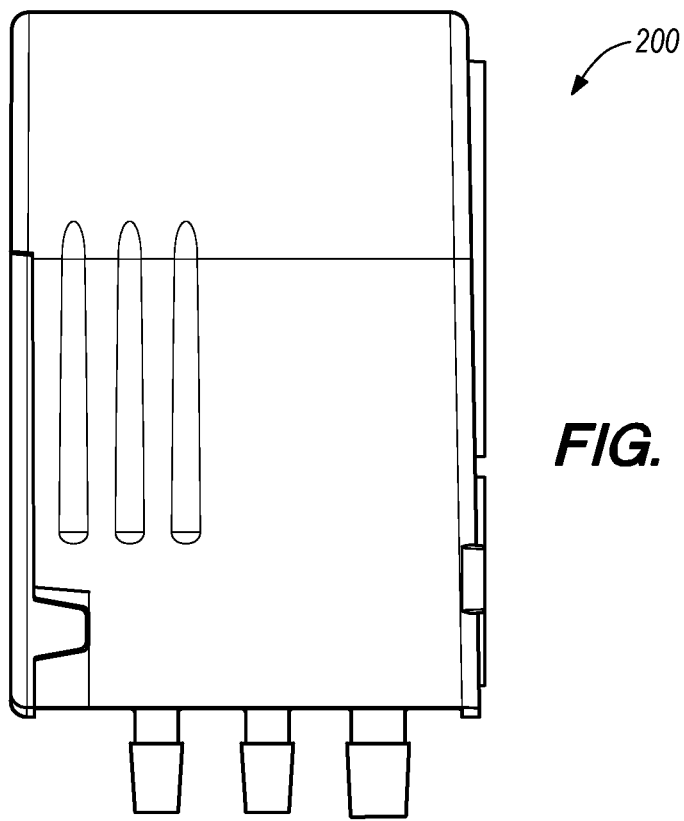
Figure 16:
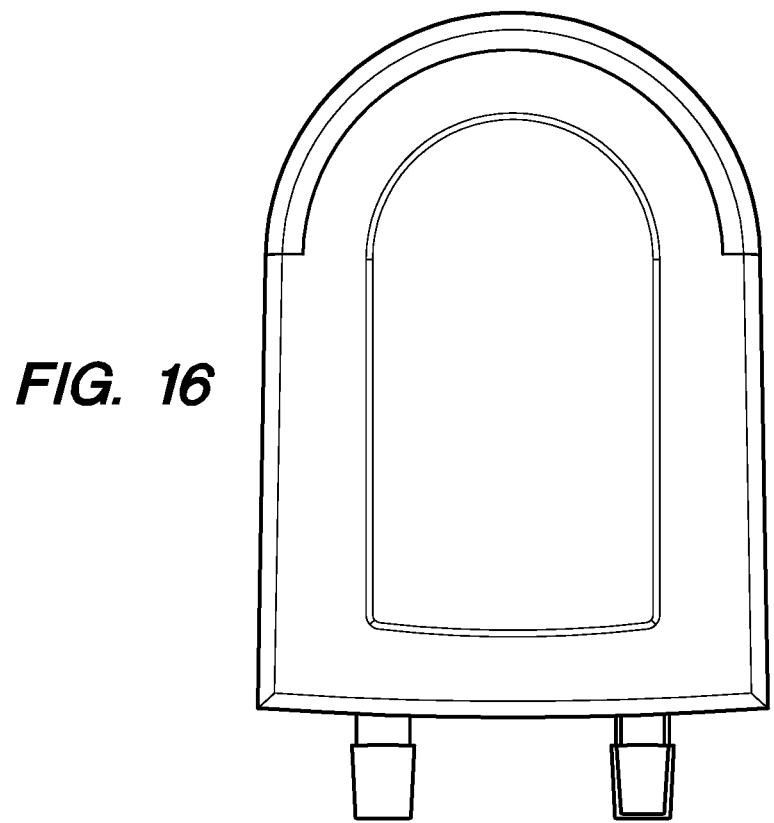
Figure 17:
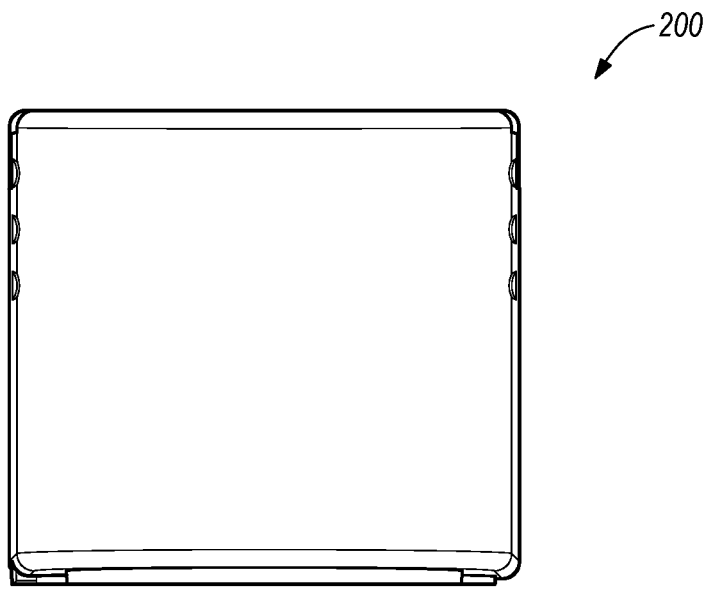
Figure 18:
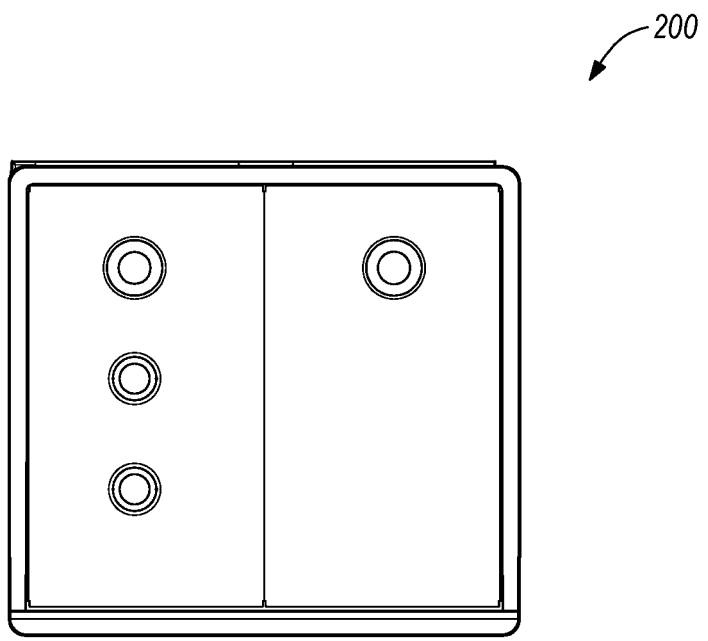
Figure 19:
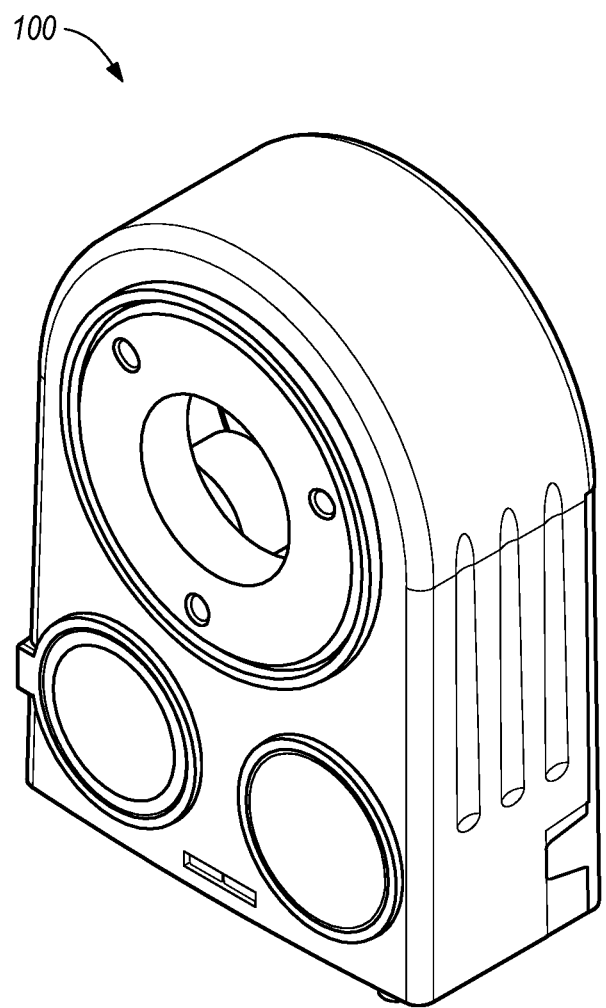
Figure 20:
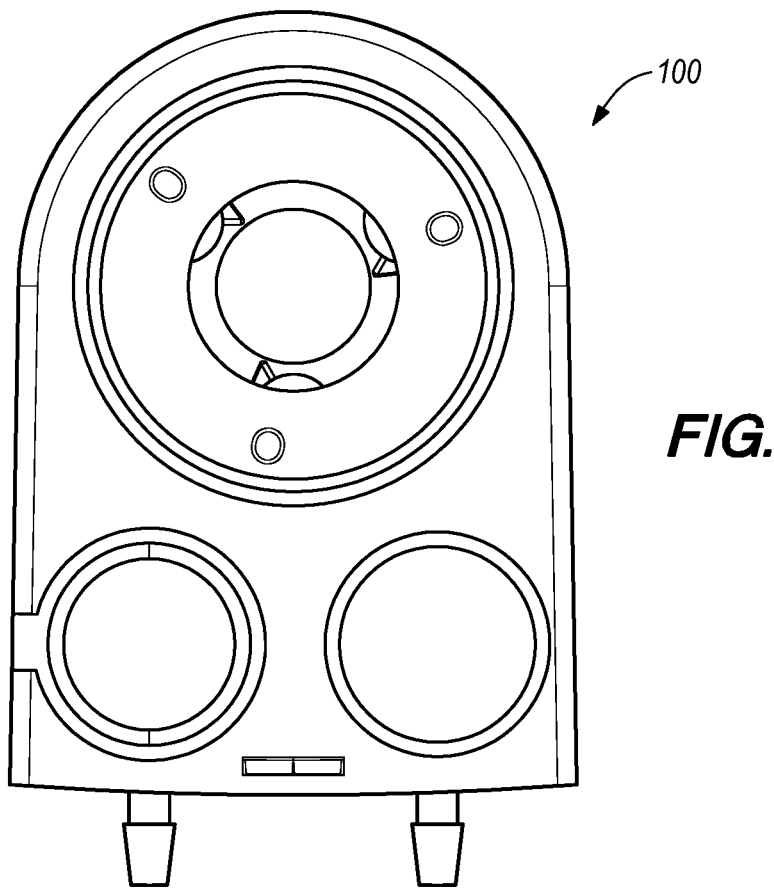
Figure 21:
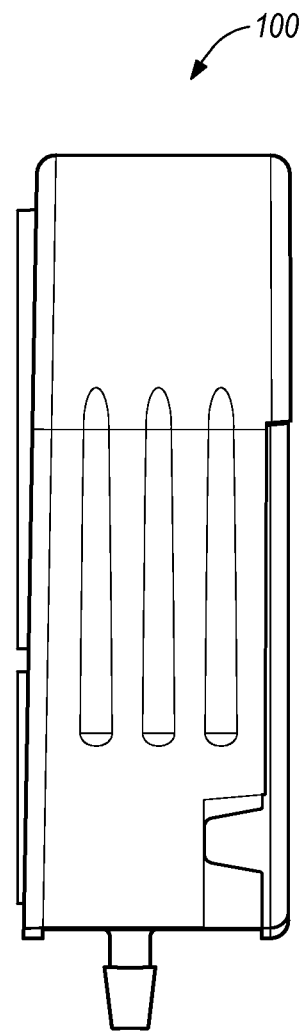
Figure 22:
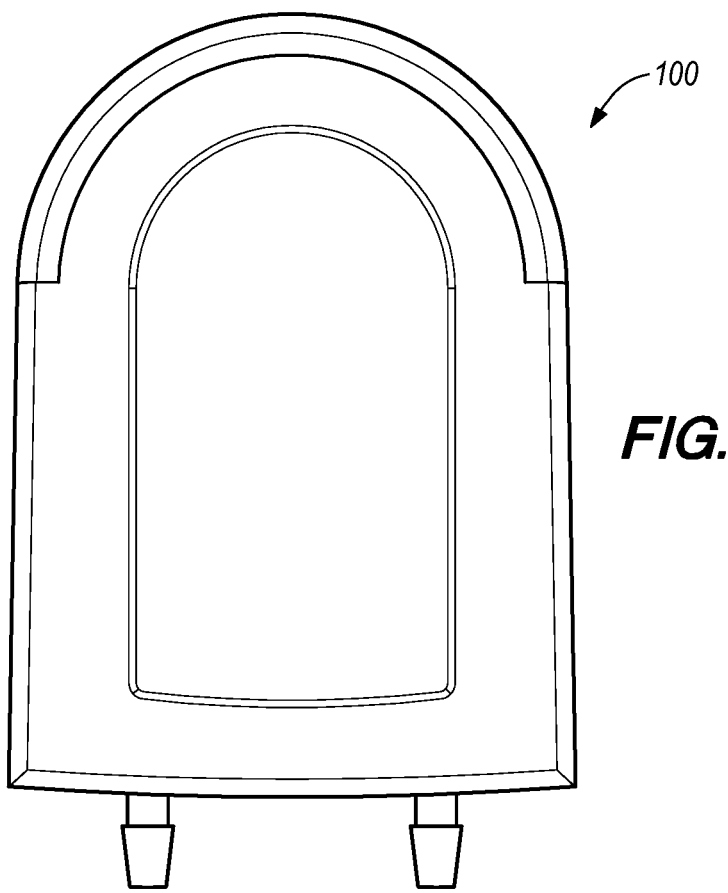
Figure 23:
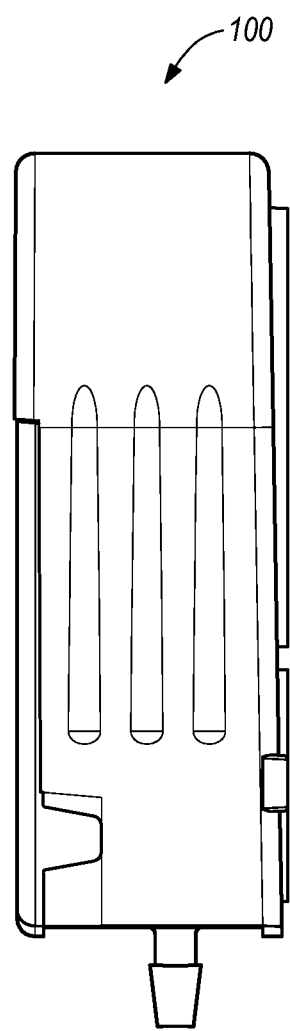
Figure 24:
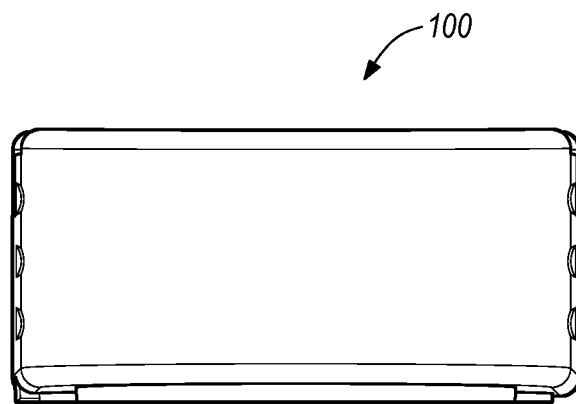
Figure 25:
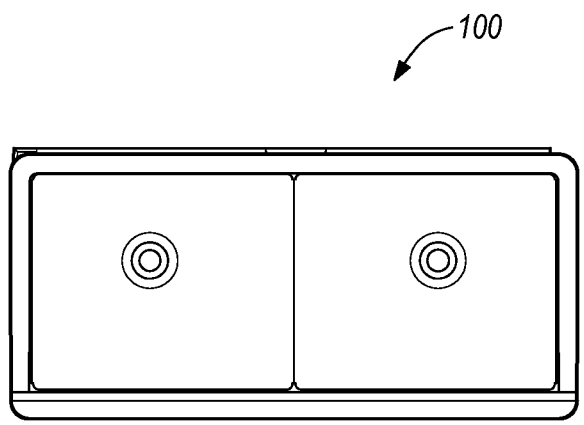

The inflow pump cartridge 100 is similar to the outflow pump cartridge 200, and is shown in more detail in FIGS. 9A and 9B. The inflow pump cartridge 100 includes a housing 112 (with an ornamental exterior configuration), a barb assembly 114, and a roller assembly 116. Since the inflow pump cartridge 100 only needs to accommodate one incoming/outgoing fluid line (e.g., the distending fluid used in the tissue removal system in U.S. Pat. No. 8,568,424), the barb assembly 114 has only one inlet barb 144, one outlet barb 146, and one internal tube 142 coupled to the inlet barb 144 and outlet barb 146. The inflow pump cartridge 100 includes a pressure sensor housing 120 disposed within an opening 126 in the housing 112. The pressure sensor housing 120 houses a pressure sensor for monitoring the flow of the source fluid. Overlying the pressure sensor housing is an inflatable bladder 123. The inflow pump cartridge 100 further includes a ferromagnetic disc 122 that fits within an opening 124 in rear face of the housing 112 (i.e., the face that mates against the console rotor) and interfaces with an electromagnet coupled to the pump console cart in the same manner as previously described with respect to the outflow pump cartridge housing.

The assembly and operation of the inflow pump cartridge 100 is similar to the assembly and operation of the outflow pump cartridge 200. During operation, the inflow pump cartridge 100 is mounted on a rotor similar to the rotor 300 discussed above and shown in FIGS. 8A and 8B. However, the rotor on which the inflow pump cartridge 100 is mounted is capable of reversing, while the rotor on which the outflow pump cartridge 200 is mounted does not require this capability.

FIGS. 10A and 10B depict an alternate embodiment of a pump console rotor 400 that may be used for driving either of the inflow and outflow pump cartridges 100 and 200, and includes a central cylindrical shaft 404 and three fins 406 protruding from the cylindrical shaft 404. The fins 406 are triangular shaped, and include a curved side extending generally radially outward for engaging the respective pump cartridge rollers, and a flat side extending tangentially from a central cylindrical shaft 404.

Although this disclosure has been provided in the context of certain embodiments and examples, it will be understood by those skilled in the art that the disclosure extends beyond the specifically disclosed embodiments to other alternative embodiments and/or uses of the embodiments and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. Thus, it is intended that the scope of the present inventions disclosed herein should not be limited to the illustrated and/or described embodiments, but are instead defined only by the claims appended hereto, and their legal equivalents.

What is claimed is:

1. A peristaltic pumping system, comprising:
    a pump console comprising a drive rotor having a roller driving feature; and a pump cartridge configured to detachably mount on the pump console, the pump cartridge comprising
  a housing having an opening through which the drive rotor extends when the pump cartridge is mounted on the pump console,
  a roller assembly disposed within the housing, the roller assembly comprising
    first and second hubs maintained in a spaced apart relationship by one or more posts extending therebetween, wherein the first and second hubs define a pump cartridge axis, and
    a plurality of planetary rollers rotatably mounted on, and extending longitudinally between, the first and second hubs, wherein the rollers are mounted in a circumferentially spaced orientation about the pump cartridge axis, and
  a barb assembly interposed between an interior wall of the housing and an outer radial periphery of the roller assembly, the barb assembly comprising one or more compressible tubing lines,
  wherein the first hub is configured to engage the roller driving feature when the pump cartridge is mounted on the pump console so that rotation of the drive rotor causes rotation of the roller assembly about the pump cartridge axis, while the pump cartridge housing remains fixed relative to the pump console.

2. The peristaltic pumping system of claim 1, wherein the roller driving feature is offset from the pump cartridge axis when the pump cartridge is mounted on the pump console.

3. A peristaltic pumping system of claim 1, comprising:
a pump console comprising a drive rotor having a roller driving feature; and
a pump cartridge configured to detachably mount on the pump console, the pump cartridge comprising
  a housing having an opening through which the drive rotor extends when the pump cartridge is mounted on the pump console,
  a roller assembly disposed within the housing, the roller assembly comprising
    first and second hubs maintained in a spaced apart relationship by one or more posts extending therebetween, wherein the first and second hubs define a pump cartridge axis, and
    a plurality of planetary rollers rotatably mounted on, and extending longitudinally between, the first and second hubs, wherein the rollers are mounted in a circumferentially spaced orientation about the pump cartridge axis, and
  a barb assembly interposed between an interior wall of the housing and an outer radial periphery of the roller assembly, the barb assembly comprising one or more compressible tubing lines,
  wherein the first hub is configured to engage the roller driving feature when the pump cartridge is mounted on the pump console so that rotation of the drive rotor causes rotation of the roller assembly about the pump cartridge axis, while the pump cartridge housing remains fixed relative to the pump console, and
  wherein the driving feature extends outwardly from an exterior facing surface of the drive rotor.

4. The peristaltic pumping system of claim 3, wherein the first hub comprises a coupling feature configured to selectively engage the roller driving feature, and wherein the coupling feature is spaced radially apart from the pump cartridge axis.

5. The peristaltic pumping system of claim 3, wherein the first hub comprises a plurality of coupling features, each coupling feature configured to selectively engage the roller driving feature.

6. The peristaltic pumping system of claim 5, wherein the plurality of coupling features comprises openings in an exterior facing surface of the first hub.

7. The peristaltic pumping system of claim 6, wherein the plurality of coupling features consists of three openings in the exterior facing surface of the first hub that are spaced substantially equal-distantly apart circumferentially about the pump cartridge axis.

8. The peristaltic pumping system of claim 6, wherein the roller driving feature comprises a spring-loaded detent mechanism configured to be at least partially depressed into the exterior facing surface of the drive rotor by the exterior facing surface of the first hub when the pump cartridge is mounted on the pump console, and wherein the detent mechanism is configured to extend into and thereby engage a respective opening in the exterior facing surface of the first hub when the drive rotor is rotated relative to the pump cartridge housing after the pump cartridge is mounted on the pump console.

9. The peristaltic pumping system of claim 8, wherein friction between the roller assembly and pump cartridge housing prevents the roller assembly from rotating relative to the pump cartridge housing when the drive rotor is rotated relative to the pump cartridge housing until the detent mechanism engages the respective opening in the exterior facing surface of the first hub.

10. The peristaltic pumping system of claim 8, the pump console comprising a sensor that detects whether the detent mechanism has engaged with the respective opening in the exterior surface of the first hub.

11. The peristaltic pumping system of claim 3, the drive rotor comprising a plurality of fins extending outwardly from the exterior surface of the drive rotor, each fin comprising first and second sides that extend radially-outwardly to an apex that extends along a length of the respective fin.

12. The peristaltic pumping system of claim 11, wherein, when the pump cartridge is mounted on the pump console, the plurality of fins structurally support the pump cartridge.

13. The peristaltic pumping system of claim 3, wherein the roller driving feature is offset from the pump cartridge axis when the pump cartridge is mounted on the pump console.

14. A pump cartridge for use in a peristaltic pumping system, the pump cartridge comprising:
a housing having an opening configured to receive a drive rotor extending from a pump console when the pump cartridge is mounted on the pump console;
a roller assembly disposed within the housing, the roller assembly comprising
  first and second hubs maintained in a spaced apart relationship by one or more posts extending therebetween, wherein the first and second hubs define a pump cartridge axis, and
  a plurality of planetary rollers rotatably mounted on, and extending longitudinally between, the first and second hubs, wherein the rollers are mounted in a circumferentially spaced orientation about the pump cartridge axis; and
a barb assembly interposed between an interior wall of the housing and an outer radially periphery of the roller assembly, the barb assembly comprising one or more compressible tubing lines, wherein the first hub is configured to engage a roller driving feature of the drive rotor and the second hub is configured to be coupled to a central shaft of the drive rotor, respectively, when the pump cartridge is mounted on the pump console, such that rotation of the drive rotor causes rotation of the roller assembly about the pump cartridge axis while the housing remains fixed relative to the pump console.

15. The pump cartridge of claim 14, further comprising an end cap coupled the second hub, wherein the end cap is configured to engage the central shaft of the drive rotor, respectively, when the pump cartridge is mounted on the pump console.

16. The pump cartridge of claim 15, wherein the end cap comprises teeth configured to engage the central shaft of the drive rotor.

17. The peristaltic pumping system of claim 14, wherein the roller driving feature is offset from the pump cartridge axis when the pump cartridge is mounted on the pump console.

* * * * *